United States Patent
Dalla-Favera et al.

(10) Patent No.: US 6,268,138 B1
(45) Date of Patent: Jul. 31, 2001

(54) RETROVIRAL VECTOR CAPABLE OF TRANSDUCING THE ALDEHYDE DEHYDROGENASE-1 GENE AND MAKING CELLS RESISTANT TO THE CHEMOTHERAPEUTIC AGENT CYCLOPHOSPHAMIDE AND ITS DERIVATIVES AND ANALOGS

(75) Inventors: Riccardo Dalla-Favera, New York, NY (US); Alessandro Massimo Gianni, Milan (IT)

(73) Assignee: The Trustees of Columbia University in the City of New York, New York, NY (US)

(*) Notice: Subject to any disclaimer, the term of this patent is extended or adjusted under 35 U.S.C. 154(b) by 0 days.

(21) Appl. No.: 09/221,294

(22) Filed: Dec. 23, 1998

Related U.S. Application Data

(63) Continuation of application No. 08/347,326, filed as application No. PCT/US94/03624 on Apr. 1, 1994, now Pat. No. 5,888,820, which is a continuation-in-part of application No. 08/041,722, filed on Apr. 1, 1993, now abandoned.

(51) Int. Cl.$^7$ ............................ C12N 9/00; C12N 15/867; C12N 15/63; C12Q 1/68; C07H 21/04

(52) U.S. Cl. ........................ 435/6; 435/320.1; 435/69.1; 435/325; 435/355; 435/357; 435/372; 435/366; 435/348; 435/252.3; 435/183; 435/189; 536/23.1; 536/23.2; 536/23.5; 536/24.3; 536/24.31

(58) Field of Search ......................... 435/320.1, 6, 69.1, 435/325, 355, 357, 372, 366, 348, 252.3, 183, 189; 536/23.1, 23.2, 23.5, 24.3, 24.31

(56) References Cited

U.S. PATENT DOCUMENTS

| | | | |
|---|---|---|---|
| 4,766,072 | * 8/1988 | Jendrisak et al. | 435/91.3 |
| 5,888,820 | 3/1999 | Dalla-Favera et al. | 435/456 |

OTHER PUBLICATIONS

Bregni, M., et al. (1992) "Human Peripheral Blood Hematopoietic Progenitors Are Optimal Targets Of Retroviral–Mediated Gene Transfer." *Blood* 80:1418–1422.
Canellos, G.P., et al. (1976) "Combination Chemotherapy For Metastatic Breast Carcinoma." *Cancer* 38:1882–1886.
Correll, P.H., et al. (1989) "Production Of Human Glucocerebrosidase In Mice After Retroviral Gene Transfer Into Multipotential Hematopoietic Progenitor Cells." *Proc. Natl. Acad. Sci. U.S.A.* 86:8912–8916.
Gianni, A.M., et al. (1989) "Granulocyte–Macrophage Colony–Stimulating Factor To Harvest Circulating Haemopoietic Stem Cells For Autotransplantation." *The Lancet* 2:580–585.
Hempel, J., et al. (1984) "Aldehyde Dehydrogenase From Human Liver." *Eur. J. BioChem.* 141:21–35.
Hsu, L.C., et al. (1989) "Genomic Structure Of The Human Cytosolic Aldehyde Dehydrogenase Gene." *Genomics* 5:857–865.
Hsu, L.C., et al. (1985) "Cloning Of cDNAs For Human Aldehyde Dehydrogenases 1 and 2." *Proc. Natl. Acad. Sci. U.S.A.* 82: 3771–3775.
Mann, R., et al. (1983) "Construction Of A Retrovirus Packaging Mutant And Its Use To Produce Helper–Free Defective Retrovirus." *Cell* 33:153–159.
Miller, A.D. and C. Buttmore (1986) "Redesign Of Retrovirus Packaging Cell Lines To Avoid Recombination Leading To Helper Virus Production." *Molecular and Cellular Biology* 6:2895–2902.
Miller, A.D. and G.J. Rosman (1989) "Improved Retroviral Vectors For Gene Transfer And Expression." *Bio Techniques* 7: 980–990.
Narayanan, R. et al. (1986) "Development of an Amphotropic, High–Titer Retrovirus Vector Expressing the Dihydrofolate Reductase Gene and Conferring Methotrexate Resistance," *Gene* 48:71–80.
Russo, J.E (1988) "Characterization of Cytosolic Aldehyde Dehydrogenase from Cyclophosphamide Resistant L1210 Cell," *Cancer Research* 48:2963–1268.
Siena, S., et al. (1989) "Circulation of CD34 Hematopoietic Stem Cells In The Peripheral Blood Of High–Dose Cyclophosphamide–Treated Patients: Enhancement By Intravenous Recombinant Human Granulocyte–Macrophage Colony–Stimulating Factor." *Blood* 74:1905–1914.
Yoshida et al. (1985) *Alcohol* 2:103–106 (Accession No. M26761).

* cited by examiner

*Primary Examiner*—David Guzo
(74) *Attorney, Agent, or Firm*—John P. White; Cooper & Dunham LLP

(57) ABSTRACT

This invention provides viral and retroviral vectors which comprises a nucleic acid molecule encoding a human cytosolic aldehyde dehydrogenase or a glutamylcysteine synthetase or combinations thereof. Further, this invention provides an isolated mammalian nucleic acid molecule encoding an cytosolic aldehyde dehydrogenase and glutamylcysteine synthetase.

In addition, this invention provides a method for reducing the toxic effects of a cyclophosphamide in a subject which comprises replacing the subject's hematopoietic cells with hematopoietic cells of having the retroviral vector.

Further, this invention provides a method for introducing a selectable marker into a mammalian cell which comprises transfecting the cell with a nucleic acid molecule encoding human cytosolic aldehyde dehydrogenase or glutamylcysteine synthetase.

Lastly, this invention provides a method for selecting mammalian cells expressing protein of interest which comprises: a). introducing into the cells a nucleic acid molecule comprising a nucleic acid molecule encoding the protein of interest and the nucleic acid molecule encoding human cytosolic aldehyde dehydrogenase; b.) culturing the resulting transfected cells; and c.) selecting cells which express human cytosolic aldehyde dehydrogenase.

14 Claims, 31 Drawing Sheets

FIGURE 2
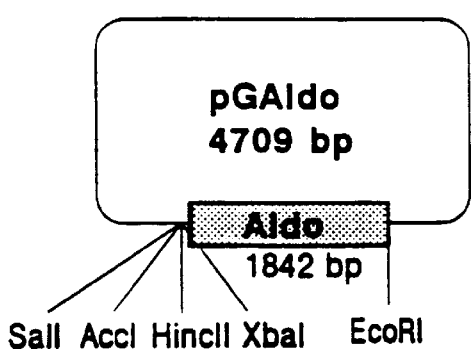
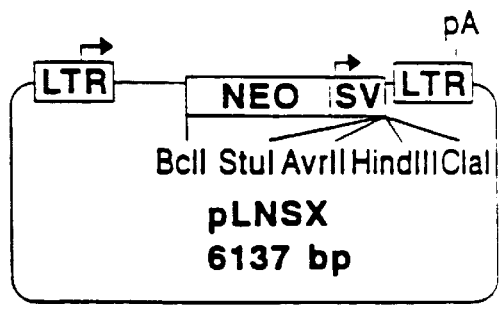
1) EcoRI + SalI DIGEST
2) FILL 3' RECESSED ENDS
3) LMP PURIFICATION
1) BclI DIGEST
2) FILL 3' RECESSED ENDS
3) StuI DIGEST
4) CIP
5) LMP PURIFICATION
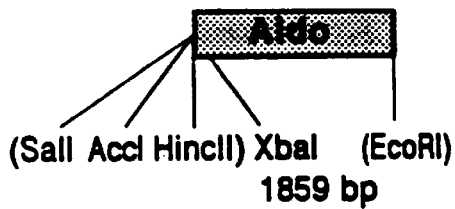
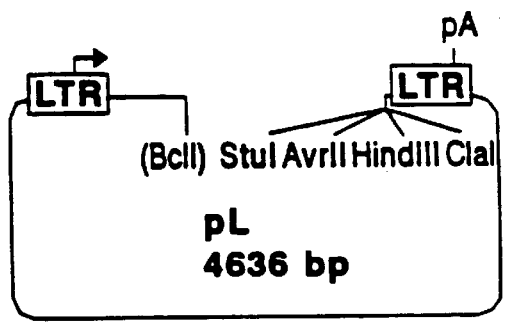
6) T4 LIGASE
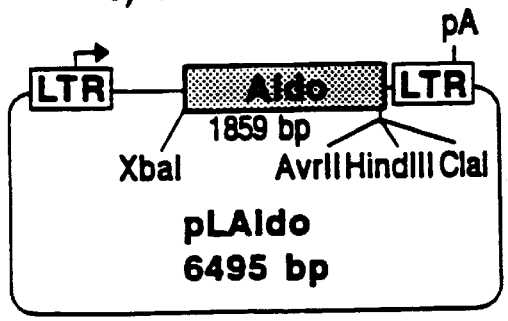

FIGURE 4-1

SEQ. ID. NO. 1

```
C TAG AAC CAA ATT GCT GAG CCA GTC ACC TGT GTT CCA GGA GCC GAA         46
    Asn Gln Ile Ala Glu Pro Val Thr Cys Val Pro Gly Ala Glu
    1               5                   10                  15

TCA GAA ATG TCA TCC TCA GGC ACG CCA GAC TTA CCT GTC CTA CTC ACC       94
Ser Glu Met Ser Ser Ser Gly Thr Pro Asp Leu Pro Val Leu Leu Thr
                20                  25                  30

GAT TTG AAG ATT CAA TAT ACT AAG ATC TTC ATA AAC AAT GAA TGG CAT       142
Asp Leu Lys Ile Gln Tyr Thr Lys Ile Phe Ile Asn Asn Glu Trp His
                35                  40                  45

GAT TCA GTG AGT GGC AAG AAA TTT CCT GTC TTT AAT CCT GCA ACT GAG       190
Asp Ser Val Ser Gly Lys Lys Phe Pro Val Phe Asn Pro Ala Thr Glu
            50                  55                  60

GAG GAG CTC TGC CAG GTA GAA GAA GGA GAT AAG GAG GAT GTT GAC AAG       238
Glu Glu Leu Cys Gln Val Glu Glu Gly Asp Lys Glu Asp Val Asp Lys
        65                  70                  75
```

FIGURE 4-2

```
GCA GTG AAG GCC GCA AGA CAG GCT TTT CAG ATT GGA TCT CCG TGG CGT    286
Ala Val Lys Ala Ala Arg Gln Ala Phe Gln Ile Gly Ser Pro Trp Arg
 80                  85                  90                  95

ACT ATG GAT GCT TCC GAG AGG CGA CTA TTA TAC AAG TTG GCT GAT        334
Thr Met Asp Ala Ser Glu Arg Arg Leu Leu Tyr Lys Leu Ala Asp
                100                 105                 110

TTA ATC GAA AGA GAT CGT CTG GCG ACA ATG GAG TCA ATG GAG TCA        382
Leu Ile Glu Arg Asp Arg Leu Ala Thr Met Glu Ser Met Glu Ser
             115                 120                 125

ATG AAT GGT GGA AAA CTC TAT TCC AAT GCA TAT CTG AAT GAT TTA GCA    430
Met Asn Gly Gly Lys Leu Tyr Ser Asn Ala Tyr Leu Asn Asp Leu Ala
                130                 135                 140

GGC TGC ATC AAA ACA TTG CGC TAC TGT GCA GGT TGG GCT GAC AAG ATC    478
Gly Cys Ile Lys Thr Leu Arg Tyr Cys Ala Gly Trp Ala Asp Lys Ile
 145                 150                 155
```

FIGURE 4-3

```
CAG GGC CAG GGC CGT ACA ATA CCA ATT GAT GGA AAT TTT ACA TAT     526
Gln Gly Gln Gly Arg Thr Ile Pro Ile Asp Gly Asn Phe Thr Tyr
160                 165                 170                 175

ACA AGA CAT GAA CCT ATT GGG GTA TGT GGC CAA ATC ATT CCT TGG AAT 574
Thr Arg His Glu Pro Ile Gly Val Cys Gly Gln Ile Ile Pro Trp Asn
        180                 185                 190

TTC CCG TTG GTT ATG CTC ATT TGG AAG ATA GGG CCT GCA CTG AGC TGT 622
Phe Pro Leu Val Met Leu Ile Trp Lys Ile Gly Pro Ala Leu Ser Cys
            195                 200                 205

GGA AAC ACA GTG GTT GTC AAA CCA GCA GAG CAA ACT CCT CTC ACT GCT 670
Gly Asn Thr Val Val Val Lys Pro Ala Glu Gln Thr Pro Leu Thr Ala
        210                 215                 220

CTC CAC GTG GCA TCT TTA ATA AAA GAG GCA GGG TTT CCT CCT GGA GTA 718
Leu His Val Ala Ser Leu Ile Lys Glu Ala Gly Phe Pro Pro Gly Val
225                 230                 235

GTG AAT ATT GTT CCT GGT TAT GGG CCT ACA GCA GGG GCA GCC ATT TCT 766
```

FIGURE 4-4

```
Val Asn Ile Val Pro Gly Tyr Gly Pro Thr Ala Gly Ala Ala Ile Ser
240                 245                 250                 255

TCT CAC ATG GAT ATA GAC AAA GTA GCC TTC ACA GGA TCA ACA GAG GTT    814
Ser His Met Asp Ile Asp Lys Val Ala Phe Thr Gly Ser Thr Glu Val
                    260                 265                 270

GGC AAG TTG ATC AAA GAA GCT GCC GGG AAA AGC AAT CTG AAG AGG GTG    862
Gly Lys Leu Ile Lys Glu Ala Ala Gly Lys Ser Asn Leu Lys Arg Val
                275                 280                 285

ACC CTG GAG CTT GGA AAG AGC CCT TGC ATT GTG TTA GCT GAT GCC        910
Thr Leu Glu Leu Gly Lys Ser Pro Cys Ile Val Leu Ala Asp Ala
            290                 295                 300

GAC TTG GAC AAT GCT GTT GAA TTT GCA CAC CAT GGG GTA TTC TAC CAC    958
Asp Leu Asp Asn Ala Val Glu Phe Ala His His Gly Val Phe Tyr His
            305                 310                 315

CAG GGC CAG TGT TGT ATA GCC GCA TCC AGG ATT TTT GTG GAA GAA TCA   1006
Gln Gly Gln Cys Cys Ile Ala Ala Ser Arg Ile Phe Val Glu Glu Ser
320                 325                 330                 335
```

FIGURE 4-5

```
ATT TAT GAT GAG TTT GTT CGA AGG AGT GTT GAG CGG GCT AAG AAG TAT    1054
Ile Tyr Asp Glu Phe Val Arg Arg Ser Val Glu Arg Ala Lys Lys Tyr
        340                 345                 350

ATC CTT GGA AAT CCT CTG ACC CCA GGA GTC ACT CAA GGC CCT CAG ATT    1102
Ile Leu Gly Asn Pro Leu Thr Pro Gly Val Thr Gln Gly Pro Gln Ile
        355                 360                 365

GAC AAG GAA CAA TAT GAT AAA ATA CTT GAC CTC ATT GAG AGT GGG AAG    1150
Asp Lys Glu Gln Tyr Asp Lys Ile Leu Asp Leu Ile Glu Ser Gly Lys
        370                 375                 380

AAA GAA GGG GCC AAA CTG GAA TGT GGA GGC CCG GGC GGG AAT AAA        1198
Lys Glu Gly Ala Lys Leu Glu Cys Gly Gly Gly Pro Gly Asn Lys
        385                 390                 395

GGC TAC TTT GTC CAG CCC ACA GTG TTC TCT AAT GTT ACA GAT GAG ATG    1246
Gly Tyr Phe Val Gln Pro Thr Val Phe Ser Asn Val Thr Asp Glu Met
        400                 405                 410             415
```

FIGURE 4-6

```
CGC ATT GCC AAA GAG GAG ATT TTT GGA CCA GTG CAG CAA ATC ATG AAG    1294
Arg Ile Ala Lys Glu Glu Ile Phe Gly Pro Val Gln Gln Ile Met Lys
            420                 425                 430

TTT AAA TCT TTA GAT GAC GTG ATC AAA AGA GCA AAC AAT ACT TTC TAT    1342
Phe Lys Ser Leu Asp Asp Val Ile Lys Arg Ala Asn Asn Thr Phe Tyr
            435                 440                 445

GGC TTA TCA GCA GGA GTG TTT ACC AAA GAC ATT GAT AAA GCC ATA ACA    1390
Gly Leu Ser Ala Gly Val Phe Thr Lys Asp Ile Asp Lys Ala Ile Thr
            450                 455                 460

ATC TCC TCT GCT CTG CAG GCA GGA ACA GTG TGG GTG AAT TGC TAT GGC    1438
Ile Ser Ser Ala Leu Gln Ala Gly Thr Val Trp Val Asn Cys Tyr Gly
            465                 470                 475

GTA AGT GCC CAG TGC CCC TTT GGT GGA TTC AAG ATG TCT GGA AAT        1486
Val Ser Ala Gln Cys Pro Phe Gly Gly Phe Lys Met Ser Gly Asn
            480                 485                 490         495

GGA AGA GAA CTG GGA GAG TAC GGT TTC CAT GAA TAT ACA GAG GTC AAA    1534
```

FIGURE 4-7

```
Gly Arg Glu Leu Gly Glu Tyr Gly Phe His Glu Tyr Thr Glu Val Lys
                500                 505                 510
ACA GTC ACA GTG AAA ATC TCT CAG AAG AAC TCA T AAAGAAAATA              1578
Thr Val Thr Val Lys Ile Ser Gln Lys Asn Ser
            515                 520

CAAGAGTGGA GAGAAGCTCT TCAATAGCTA AGCATCTCCT TACAGTCACT AATATAGTAG    1638
ATTTTAAAGA CAAAATTTTT CTTTTCTTGA TTTTTTTTAA ACATAAGCTA AATCATATTA    1698
GTATTAATAC TACCCATAGA AAACTTGACA TGTAGCTTCT TCTGAAAGAA TTATTTGCCT    1758
TCTGAAATGT GACCCCCAAG TCCTATCCTA AATAAAAAAA GACAAATTCG GATGTATGAT    1818
CTCTCTAGCT TTGTCATAGT TATG                                           1842
```

FIGURE 5-1

SEQ. ID. NO. 2

```
Asn Gln Ile Ala Glu Pro Val Thr Cys Val Thr Pro Gly Ala Glu Ser
 1                   5                  10                  15
Glu Met Ser Ser Ser Gly Thr Pro Asp Leu Pro Val Leu Leu Thr Asp
                    20                  25                  30
Leu Lys Ile Gln Tyr Thr Lys Ile Phe Ile Asn Asn Glu Trp His Asp
                    35                  40                  45
Ser Val Ser Gly Lys Lys Phe Pro Val Phe Asn Pro Ala Thr Glu Glu
                    50                  55                  60
Glu Leu Cys Gln Val Glu Glu Gly Asp Lys Glu Asp Val Asp Lys Ala
                    65                  70                  75                  80
Val Lys Ala Ala Arg Gln Ala Phe Gln Ile Gly Ser Pro Trp Arg Thr
                    85                  90                  95
```

FIGURE 5-2

```
Met Asp Ala Ser Glu Arg Gly Arg Leu Leu Tyr Lys Leu Ala Asp Leu
                100                 105                 110

Ile Glu Arg Asp Arg Leu Leu Ala Leu Tyr Ser Asn Ala Ser Met Glu Ser Met
        115                 120                 125

Asn Gly Gly Lys Leu Tyr Ser Asn Ala Tyr Leu Asn Asp Leu Ala Gly
        130                 135                 140

Cys Ile Lys Thr Leu Arg Tyr Cys Ala Gly Trp Ala Asp Lys Ile Gln
    145                 150                 155                 160

Gly Gln Gly Arg Thr Ile Pro Ile Asp Gly Asn Phe Phe Thr Tyr Thr
                165                 170                 175

Arg His Glu Pro Ile Gly Val Cys Gly Gln Ile Ile Pro Trp Asn Phe
        180                 185                 190
```

FIGURE 5-3

Pro Leu Val Met Leu Ile Trp Lys Ile Gly Pro Ala Leu Ser Cys Gly
                195                 200                 205

Asn Thr Val Val Val Lys Pro Ala Glu Gln Thr Pro Leu Thr Ala Leu
        210                 215                 220

His Val Ala Ser Leu Ile Lys Glu Ala Gly Phe Pro Pro Gly Val Val
225                 230                 235                 240

Asn Ile Val Pro Gly Tyr Gly Pro Thr Ala Gly Ala Ala Ile Ser Ser
            245                 250                 255

His Met Asp Ile Asp Lys Val Ala Phe Thr Gly Ser Thr Glu Val Gly
        260                 265                 270

Lys Leu Ile Lys Glu Ala Ala Gly Lys Ser Asn Leu Lys Arg Val Thr
    275                 280                 285

Leu Glu Leu Gly Gly Lys Ser Pro Cys Ile Val Leu Ala Asp Ala Asp
290                 295                 300

FIGURE 5-4

Leu Asp Asn Ala Val Glu Phe Ala His His Gly Val Phe Tyr His Gln
305                     310                    315                    320

Gly Gln Cys Cys Ile Ala Ala Ser Arg Ile Phe Val Glu Glu Ser Ile
325                     330                    335

Tyr Asp Glu Phe Val Arg Arg Ser Val Glu Arg Ala Lys Lys Tyr Ile
340                     345                    350

Leu Gly Asn Pro Leu Thr Pro Gly Val Thr Gln Gly Pro Gln Ile Asp
355                     360                    365

Lys Glu Gln Tyr Asp Lys Ile Leu Asp Leu Ile Glu Ser Gly Lys Lys
370                     375                    380

Glu Gly Ala Lys Leu Glu Cys Gly Gly Gly Pro Trp Gly Asn Lys Gly
385                     390                    395                    400

Tyr Phe Val Gln Pro Thr Val Phe Ser Asn Val Thr Asp Glu Met Arg
405                     410                    415

FIGURE 5-5

Ile Ala Lys Glu Glu Ile Phe Gly Pro Val Gln Gln Ile Met Lys Phe
420                                425                            430

Lys Ser Leu Asp Asp Val Ile Lys Arg Ala Asn Asn Thr Phe Tyr Gly
435                                440                            445

Leu Ser Ala Gly Val Phe Thr Lys Asp Ile Asp Lys Ala Ile Thr Ile
450                                455                            460

Ser Ser Ala Leu Gln Ala Gly Thr Val Trp Val Asn Cys Tyr Gly Val
465                                470                       475                  480

Val Ser Ala Gln Cys Pro Phe Gly Gly Phe Lys Met Ser Gly Asn Gly
                485                            490                            495

Arg Glu Leu Gly Glu Tyr Gly Phe His Glu Tyr Thr Glu Val Lys Thr
500                                505                            510

Val Thr Val Lys Ile Ser Gln Lys Asn Ser
515                                520

FIGURE 6-1
SEQ. ID. NO.3

```
GAATTCCGGG CGGGAGCCGC CGCGGCAGCG CGGCCGGTGGG GTCCGCCGCC GCCGCATCGG    60
AGCGGGAGGA GGAGCAGCGG GGAGGGCGAG GCCGCCGGGC CGAGAGCCGT CCCGCCTGCT   120
CTCGGTCTTC TGCCTTCGCC TCCGCGGGT GCGTCGGACC CAGGGTCTGT CACCTGGGCG   180
CCAGGGGCCG CCCGCCGGGA GCCGGAGCGG GCAGGACCCT CCCTCCGCCG ACTGCGGCCC   240
GAGAGCGCCC CCGCGGGGTG GAGCGGCAGC CGCCTTCTGC GGGCGGGCTGA GTGTCCGTCT  300
CGCGCCCGGA GCGGGCGACC GCCGTCAGCC CGGAGGAGGA GGAGGAGGAG GAGGGGGCGT   360
CC ATG GGG CTG CTG CTG TCC CAG GGC TCG CCG CTG AGC TGG GAG GAA ACC  407
   Met Gly Leu Leu Leu Ser Gln Gly Ser Pro Leu Ser Trp Glu Glu Thr
   1               5                  10                  15
AAG CGC CAT GCC GAC CAC GTG CGG CGG CAC GGG ATC CTC CAG TTC CTG    455
Lys Arg His Ala Asp His Val Arg Arg His Gly Ile Leu Gln Phe Leu
                20                  25                  30
```

FIGURE 6-2

```
                                                                          503
CAC ATC TAC CAC GCC GTC AAG GAC CGG CAC AAG GAC GTT CTC AAG TGG
His Ile Tyr His Ala Val Lys Asp Arg His Lys Asp Val Leu Lys Trp
         35                  40                  45

551
GGC GAT GAG GTG GAA TAC ATG TTG GTA TCT TTT GAT CAT GAA AAT AAA
Gly Asp Glu Val Glu Tyr Met Leu Val Ser Phe Asp His Glu Asn Lys
     50                  55                  60

599
AAA GTC CGG TTG GTC CTG TCT GGG GAG AAA GTT CTT GAA ACT CTG CAA
Lys Val Arg Leu Val Leu Ser Gly Glu Lys Val Leu Glu Thr Leu Gln
         65                  70                  75

647
GAG AAG GGG GAA AGG ACA AAC CAT CCT ACC CTT TGG AGA CCA
Glu Lys Gly Glu Arg Thr Asn His Pro Thr Leu Trp Arg Pro
     80                  85                  90              95

695
GAG TAT GGG AGT TAC ATG ATT GAA GGG ACA CCA GGA CAG CCC TAC GGA
Glu Tyr Gly Ser Tyr Met Ile Glu Gly Thr Pro Gly Gln Pro Tyr Gly
         100                 105                     110

743
GGA ACA ATG TCC GAG TTC AAT ACA GTT GAG GCC AAC ATG CGA AAA CGC
```

FIGURE 6-3

```
                        Gly Thr Met Ser Glu Phe Asn Thr Val Glu Ala Asn Met Arg Lys Arg
                                        115                 120                 125
791  CGG AAG GAG GCT ACT TCT ATA TTA GAA GAA AAT CAG GCT CTT TGC ACA
     Arg Lys Glu Ala Thr Ser Ile Leu Glu Glu Asn Gln Ala Leu Cys Thr
                     130                 135                 140
839  ATA ACT TCA TTT CCC AGA TTA GGC TGT CCT GGG TTC ACA CTG CCC GAG
     Ile Thr Ser Phe Pro Arg Leu Gly Cys Pro Gly Phe Thr Leu Pro Glu
                     145                 150                 155
887  GTC AAA CCC AAC CCA GTG GAA GGA GCT TCC AAG TCC CTC TTC TTT
     Val Lys Pro Asn Pro Val Glu Gly Ala Ser Lys Ser Leu Phe Phe
                     160                 165         170         175
935  CCA GAT GAA GCA ATA AAC AAG CAC CCT CGC TTC AGT ACC TTA ACA AGA
     Pro Asp Glu Ala Ile Asn Lys His Pro Arg Phe Ser Thr Leu Thr Arg
                     180                 185                 190
983  AAT ATC CGA CAT AGG AGA GGA GAA AAG GTT GTC ATC AAT CTA CCA ATA
     Asn Ile Arg His Arg Arg Gly Glu Lys Val Val Ile Asn Leu Pro Ile
                     195                 200                 205
```

FIGURE 6-4

```
TTT AAG GAC AAG AAT ACA CCA TCT CCA TTT ATA GAA ACA TTT ACT GAG      1031
Phe Lys Asp Lys Asn Thr Pro Ser Pro Phe Ile Glu Thr Phe Thr Glu
    210                 215                 220

GAT GAA GCT TCA AGG GCT TCT AAG CCG GAT CAT ATT TAC ATG GAT          1079
Asp Glu Ala Ser Arg Ala Ser Lys Pro Asp His Ile Tyr Met Asp
225                 230                 235

GCC ATG GGA TTT GGA ATG GGC AAT TGC TGT CTC CAG GTG ACA TTC CAA      1127
Ala Met Gly Phe Gly Met Gly Asn Cys Cys Leu Gln Val Thr Phe Gln
240                 245                 250                 255

GCC TGC AGT ATA TCT GAG GCC AGA TAC CTT TAT GAT CAG TTG GCT ACT      1175
Ala Cys Ser Ile Ser Glu Ala Arg Tyr Leu Tyr Asp Gln Leu Ala Thr
        260                 265                 270

ATC TGT CCA ATT GTT ATG GCT TTG AGT GCT GCA TCT CCC TTT TAC CGA      1223
Ile Cys Pro Ile Val Met Ala Leu Ser Ala Ala Ser Pro Phe Tyr Arg
275                 280                 285
```

FIGURE 6-5

```
GGC TAT GTG TCA GAC ATT GAT TGT CGC TGG GGA GTG ATT TCT GCA TCT    1271
Gly Tyr Val Ser Asp Ile Asp Cys Arg Trp Gly Val Ile Ser Ala Ser
290                         295                 300

GTA GAT GAT AGA ACT CGG GAG GAG CGA GGA CTG GAG CCA TTG AAG AAC    1319
Val Asp Asp Arg Thr Arg Glu Glu Arg Gly Leu Glu Pro Leu Lys Asn
305                         310                 315

AAT AAC TAT AGG ATC AGT AAA TCC CGA TAT GAC TCA ATA GAC AGC TAT    1367
Asn Asn Tyr Arg Ile Ser Lys Ser Arg Tyr Asp Ser Ile Asp Ser Tyr
320                         325                 330             335

TTA TCT AAG TGT GGT GAG AAA TAT AAT GAC ATC GAC TTG ACG ATA GAT    1415
Leu Ser Lys Cys Gly Glu Lys Tyr Asn Asp Ile Asp Leu Thr Ile Asp
                340                         345                 350

AAA GAG ATC TAC GAA CAG CTG TTG CAG GAA GGC ATT GAT CAT CTC CTG    1463
Lys Glu Ile Tyr Glu Gln Leu Leu Gln Glu Gly Ile Asp His Leu Leu
        355                         360                 365

GCC CAG CAT GTT GCT CAT CTC TTT ATT AGA GAC CCA CTG ACA CTG TTT    1511
```

FIGURE 6-6

```
Ala Gln His Val Ala His Leu Phe Ile Arg Asp Pro Leu Thr Leu Phe
        370                 375                 380

GAA GAG AAA ATA CAC CTG GAT GAT GCT AAT GAG TCT GAC CAT TTT GAG    1559
Glu Glu Lys Ile His Leu Asp Asp Ala Asn Glu Ser Asp His Phe Glu
        385                 390                 395

AAT ATT CAG TCC ACA AAT TGG CAG ACA ATG AGA TTT AAG CCC CCT CCT    1607
Asn Ile Gln Ser Thr Asn Trp Gln Thr Met Arg Phe Lys Pro Pro Pro
        400                 405                 410            415

CCA AAC TCA GAC ATT GGA TGG AGA GTA GAA TTT CGA CCC ATG GAG GTG    1655
Pro Asn Ser Asp Ile Gly Trp Arg Val Glu Phe Arg Pro Met Glu Val
        420                 425                 430

CAA TTA ACA GAC TTT GAG AAC TCT GCC TAT GTG GTG TTT GTG GTA CTG    1703
Gln Leu Thr Asp Phe Glu Asn Ser Ala Tyr Val Val Phe Val Val Leu
        435                 440                 445

CTC ACC AGA GTG ATC CTT TCC TAC AAA TTG GAT TTT CTC ATT CCA CTG    1751
Leu Thr Arg Val Ile Leu Ser Tyr Lys Leu Asp Phe Leu Ile Pro Leu
        450                 455                 460
```

FIGURE 6-7

```
TCA AAG GTT GAT GAG AAC ATG AAG GTA GCA CAG AAA AGA GAT GCT GTC   1799
Ser Lys Val Asp Glu Asn Met Lys Val Ala Gln Lys Arg Asp Ala Val
465                         470                 475

TTG CAG GGA ATG TTT TAT TTC AGG AAA GAT ATT TGC AAA GGT GGC AAT   1847
Leu Gln Gly Met Phe Tyr Phe Arg Lys Asp Ile Cys Lys Gly Gly Asn
480                 485                 490                 495

GCA GTG GTG GAT GGT TGT GGC AAG GCC CAG AAC AGC ACG GAG CTC GCT   1895
Ala Val Val Asp Gly Cys Gly Lys Ala Gln Asn Ser Thr Glu Leu Ala
            500                 505                 510

GCA GAG GAG TAC ACC CTC ATG AGC ATA GAC ACC ATC ATC AAT GGG AAG   1943
Ala Glu Glu Tyr Thr Leu Met Ser Ile Asp Thr Ile Ile Asn Gly Lys
        515                 520                 525

GAA GGT GTG TTT CCT GGA CTG ATC CCA ATT CTG AAC TCT TAC CTT GAA   1991
Glu Gly Val Phe Pro Gly Leu Ile Pro Ile Leu Asn Ser Tyr Leu Glu
    530                 535                 540
```

FIGURE 6-8

```
AAC ATG GAA GTG GAT GTG GAC ACC AGA TGT AGT ATT CTG AAC TAC CTA    2039
Asn Met Glu Val Asp Val Asp Thr Arg Cys Ser Ile Leu Asn Tyr Leu
545                 550                 555

AAG CTA ATT AAG AAG AGA TCT GGA GAA CTA ATG ACA GTT GCC AGA        2087
Lys Leu Ile Lys Lys Arg Ala Ser Gly Glu Leu Met Thr Val Ala Arg
560                 565                 570                 575

TGG ATG AGG GAG TTT ATC GCA AAC CAT CCT GAC TAC AAG CAA GAC AGT    2135
Trp Met Arg Glu Phe Ile Ala Asn His Pro Asp Tyr Lys Gln Asp Ser
        580                 585                 590

GTC ATA ACT GAT GAA ATG AAT TAT AGC CTT ATT TTG AAG TGT AAC CAA    2183
Val Ile Thr Asp Glu Met Asn Tyr Ser Leu Ile Leu Lys Cys Asn Gln
        595                 600                 605

ATT GCA AAT GAA TTA TGT GAA TGC CCA GAG TTA CTT GGA TCA GCA TTT    2231
Ile Ala Asn Glu Leu Cys Glu Cys Pro Glu Leu Leu Gly Ser Ala Phe
610                 615                 620

AGG AAA GTA AAA TAT AGT GGA AGT AAA ACT GAC TCA TCC AAC T          2274
```

FIGURE 6-9

```
Arg Lys Val Lys Tyr Ser Gly Ser Lys Thr Asp Ser Ser Asn
             625                 630                 635

AGACATTCTA CAGAAAGAAA AATGCATTAT TGACGAACTG GCTACAGTAC CATGCCTCTC    2334
AGCCCGTGTG TATAATATGA AGACCAAATG ATAGAACTGT ACTGTTTCT GGGCCAGTGA     2394
GCCAGAAATT GATTAAGGCT TTCTTTGGTA GAGTTTATAC AGTGTACATG               2454
TACATAGTAA AGTATTTTG ATTAACAATG TATTTTAATA ACATATCTAA AGTCATCATG     2514
AACTGGCTTG TACATTTTA AATTCTTACT CTGGAGCAAC CTACTGTCTA AGCAGTTTTG     2574
TAAATGTACT CAATACTTGC ATTCCAGAGT TAAAATGTTT ACTGTAAATT               2634
TTTGTTCTTT TAAAGACTAC CTGGGACCTG ATTTATTGAA ATTTTTCT TTAAAAACAT      2694
TTTCTCTCGT TAATTTTCCT TTGTCATTTC CTTTGTTGTC TACATTAAAT CACTTGAATC    2754
CATTGAAAGT GCTTCAAGGG TAATCTTGGG TTTCTAGCAC CTTATCTATG ATGTTTCTTT    2814
TGCAATTGGA ATAATCACTT GGTCACCTTG CCCCAAGCTT TCCCCTCTGA ATAAATACCC    2874
ATTGAACTCT GAAAAAAAAA AAAAAAAAA                                     2904
```

FIGURE 7-1

SEQ. ID. NO. 4

```
Met Gly Leu Leu Ser Gln Gly Ser Pro Leu Ser Trp Glu Glu Thr Lys
 1                   5                  10                  15

Arg His Ala Asp His Val Arg Arg His Gly Ile Leu Gln Phe Leu His
                    20                  25                  30

Ile Tyr His Ala Val Lys Asp Arg His Lys Asp Val Leu Lys Trp Gly
                    35                  40                  45

Asp Glu Val Glu Tyr Met Leu Val Ser Phe Asp His Glu Asn Lys Lys
                    50                  55                  60

Val Arg Leu Val Leu Ser Gly Glu Lys Val Leu Glu Thr Leu Gln Glu
 65                 70                  75                  80
```

FIGURE 7-2

Lys Gly Glu Arg Thr Asn Pro Asn His Pro Thr Leu Trp Arg Pro Glu
                85                  90                  95

Tyr Gly Ser Tyr Met Ile Glu Gly Thr Pro Gly Gln Pro Tyr Gly Gly
                100                 105                 110

Thr Met Ser Glu Phe Asn Thr Val Glu Ala Asn Met Arg Lys Arg Arg
                115                 120                 125

Lys Glu Ala Thr Ser Ile Leu Glu Glu Asn Gln Ala Leu Cys Thr Ile
                130                 135                 140

Thr Ser Phe Pro Arg Leu Gly Cys Pro Gly Phe Thr Leu Pro Glu Val
                145                 150                 155                 160

FIGURE 7-3

Lys Pro Asn Pro Val Glu Gly Gly Ala Ser Lys Ser Leu Phe Phe Pro
165                                170                           175

Asp Glu Ala Ile Asn Lys His Pro Arg Phe Ser Thr Leu Thr Arg Asn
180                               185                           190

Ile Arg His Arg Arg Gly Glu Lys Val Val Ile Asn Leu Pro Ile Phe
195                               200                           205

Lys Asp Lys Asn Thr Pro Ser Pro Phe Ile Glu Thr Phe Thr Glu Asp
210                               215                           220

Asp Glu Ala Ser Arg Ala Ser Lys Pro Asp His Ile Tyr Met Asp Ala
225                               230                           235                           240

Met Gly Phe Gly Met Gly Asn Cys Cys Leu Gln Val Thr Phe Gln Ala
245                               250                           255

Cys Ser Ile Ser Glu Ala Arg Tyr Leu Tyr Asp Gln Leu Ala Thr Ile
260                               265                           270

Cys Pro Ile Val Met Ala Leu Ser Ala Ala Ser Pro Phe Tyr Arg Gly
275                               280                           285

FIGURE 7-4

```
Tyr Val Ser Asp Ile Asp Cys Arg Trp Gly Val Ile Ser Ala Ser Val
290                 295                 300                 
Asp Asp Arg Thr Arg Glu Glu Arg Gly Leu Glu Pro Leu Lys Asn Asn
305                 310                 315                 320
Asn Tyr Arg Ile Ser Lys Ser Arg Tyr Asp Ser Ile Asp Ser Tyr Leu
                325                 330                 335
Ser Lys Cys Gly Glu Lys Tyr Asn Asp Ile Asp Leu Thr Ile Asp Lys
                340                 345                 350
Glu Ile Tyr Glu Gln Leu Leu Gln Glu Gly Ile Asp His Leu Leu Ala
                355                 360                 365
Gln His Val Ala His Leu Phe Ile Arg Asp Pro Leu Thr Leu Phe Glu
370                 375                 380                 
Glu Lys Ile His Leu Asp Asp Ala Asn Glu Ser Asp His Phe Glu Asn
385                 390                 395                 400
```

FIGURE 7-5

Ile Gln Ser Thr Asn Trp Gln Thr Met Arg Phe Lys Pro Pro Pro
                        405                 410                 415

Asn Ser Asp Ile Gly Trp Arg Val Glu Phe Arg Pro Met Glu Val Gln
                        420                 425                 430

Leu Thr Asp Phe Glu Asn Ser Ala Tyr Val Val Phe Val Val Leu Leu
                        435                 440                 445

Thr Arg Val Ile Leu Ser Tyr Lys Leu Asp Phe Leu Ile Pro Leu Ser
                        450                 455                 460

Lys Val Asp Glu Asn Met Lys Val Ala Gln Lys Arg Asp Ala Val Leu
                        465                 470                 475                 480

Gln Gly Met Phe Tyr Phe Arg Lys Asp Ile Cys Lys Gly Gly Asn Ala
                        485                 490                 495

Val Val Asp Gly Cys Gly Lys Ala Gln Asn Ser Thr Glu Leu Ala Ala

FIGURE 7-6

Glu Glu Tyr Thr Leu Met Ser Ile Asp Thr Ile Ile Asn Gly Lys Glu
500                 515                 520                 525                 510

Gly Val Phe Pro Gly Leu Ile Pro Ile Leu Asn Ser Tyr Leu Glu Asn
            530                 535                 540

Met Glu Val Asp Val Asp Thr Arg Cys Ser Ile Leu Asn Tyr Leu Lys
545                 550                 555                 560

Leu Ile Lys Lys Arg Ala Ser Gly Glu Leu Met Thr Val Ala Arg Trp
                565                 570                 575

Met Arg Glu Phe Ile Ala Asn His Pro Asp Tyr Lys Gln Asp Ser Val
            580                 585                 590

Ile Thr Asp Glu Met Asn Tyr Ser Leu Ile Leu Lys Cys Asn Gln Ile
        595                 600                 605

Ala Asn Glu Leu Cys Glu Cys Pro Glu Leu Leu Gly Ser Ala Phe Arg
            610                 615                 620

Lys Val Lys Tyr Ser Gly Ser Lys Thr Asp Ser Ser Asn
625                 630                 635

US 6,268,138 B1

RETROVIRAL VECTOR CAPABLE OF TRANSDUCING THE ALDEHYDE DEHYDROGENASE-1 GENE AND MAKING CELLS RESISTANT TO THE CHEMOTHERAPEUTIC AGENT CYCLOPHOSPHAMIDE AND ITS DERIVATIVES AND ANALOGS

This application is a continuation of U.S. Ser. No. 08/347,326, filed on Dec. 1, 1994, now U.S. Pat. No. 5,888,820, which is a 371 of PCT/US94/03624, filed Apr. 1, 1994 which is a continuation-in-part of U.S. application Ser. No. 08/041,722, filed on Apr. 1, 1993, now abandoned the contents of which are hereby incorporated by reference.

Throughout this application various publications are referenced by the names of the authors and the year of the publication within parentheses. Full citations for these publications may be found at the end of the specification immediately preceding the claims. The disclosures of these publications in their entireties are hereby incorporated by reference into this application in order to more fully describe the state of the art to which this invention pertains.

BACKGROUND OF INVENTION

Recent advances in autologous bone marrow transplant strategies indicate that normal hematopoiesis can be promptly restored in patients treated with myelotoxic agents (drugs or radiation) by re-injection of autologous peripheral blood (CD34$^+$) "stem cells" (Gianni, et al., Lancet 2:580, 1989). In addition, it has very recently been reported that CD34$^+$ cells can be transduced in vitro at high efficiency with retroviral vectors expressing specific genes (Bregni, et al., Blood 80:1418, 1992). These technology open the way to approaches in which the in vitro transduction of specific genes into autologous CD34$^+$ cells followed by reinoculation into patients can be used to transduce genes of therapeutic significance. This gene therapy approach includes the reconstitution of drug-resistant hematopoietic cells allowing for subsequent treatment with higher dose myelotoxic chemotherapy in cancer patients.

SUMMARY OF INVENTION

This invention provides a vector which comprises a nucleic acid molecule encoding a human cytosolic aldehyde dehydrogenase.

In addition, this invention provides a vector which comprises a nucleic acid molecule encoding a human glutamylcysteine synthetase.

In addition, this invention provides a retroviral vector, which comprises a nucleic acid molecule encoding a human cytosolic aldehyde dehydrogenase.

In addition, this invention provides a retroviral vector, which comprises a nucleic acid molecule encoding a human glutamylcysteine synthetase.

In addition, this invention provides a vector, which comprises a nucleic acid molecule encoding a human cytosolic aldehyde dehydrogenase and a glutamylcysteine synthetase.

In addition, this invention provides a method for reducing the toxic effects of a cyclophosphamide in a subject which comprises replacing the subject's hematopoietic cells with hematopoietic cells of having the retroviral vector which comprises a nucleic acid molecule encoding a human cytosolic aldehyde dehydrogenase so as to reduce the toxic effects of the cyclophosphamide in the subject.

In addition, this invention provides a method for introducing a selectable marker into a mammalian cell which comprises transfecting the cell with a nucleic acid molecule encoding a human cytosolic aldehyde dehydrogenase.

In addition, this invention provides a method for selecting mammalian cells expressing protein of interest which comprises: a). introducing into the cells a nucleic acid molecule comprising a nucleic acid molecule encoding the protein of interest and the nucleic acid molecule encoding human cytosolic aldehyde dehydrogenase; b.) culturing the resulting transfected cells; and c.) selecting cells which express human cytosolic aldehyde dehydrogenase, so as to obtain cells which express the protein of interest.

In addition, this invention provides a method for reducing the toxic effects of a cyclophosphamide in a subject which comprises replacing the subject's hematopoietic cells with hematopoietic cells of having the retroviral vector which comprises a nucleic acid molecule encoding a human glutamylcysteine synthetase so as to reduce the toxic effects of the cyclophosphamide in the subject.

In addition, this invention provides a method for introducing a selectable marker into a mammalian cell which comprises transfecting the cell with a nucleic acid molecule encoding human glutamylcysteine synthetase.

In addition, this invention provides a method for selecting mammalian cells expressing protein of interest which comprises: a). introducing into the cells a nucleic acid molecule comprising a nucleic acid molecule encoding the protein of interest and the nucleic acid molecule encoding human glutamylcysteine synthetase; b.) culturing the resulting transfected cells; and c.) selecting cells which express human glutamylcysteine synthetase, so as to obtain cells which express the protein of interest.

In addition, this invention provides an isolated mammalian nucleic acid molecule encoding a cytosolic aldehyde dehydrogenase. The isolated mammalian nucleic acid molecule may have substantially the same sequence shown in FIG. 4 (SEQ ID NO: 1).

In addition, this invention provides an isolated mammalian nucleic acid molecule encoding a glutamylcysteine synthetase. The isolated mammalian nucleic acid molecule may have substantially the same sequence shown in FIG. 6 (SEQ ID NO: 3).

In addition, this invention provides a nucleic acid molecule of at least 15 nucleotides capable of specifically hybridizing with a sequence of the nucleic acid molecule of the isolated mammalian nucleic acid molecule encoding an cytosolic aldehyde dehydrogenase or a glutamylcysteine synthetase.

In addition, this invention provides a method of detecting expression of an aldehyde dehydrogenase in a cell which comprises obtaining total mRNA from the cell, contacting the mRNA so obtained with a labelled nucleic acid molecule of the isolated mammalian nucleic acid molecule encoding an cytosolic aldehyde dehydrogenase under hybridizing conditions, determining the presence of mRNA hybridized to the molecule, and thereby detecting the expression of the cytosolic aldehyde dehydrogenase in the cell.

In addition, this invention provides a method of producing a polypeptide having the biological activity of a mammalian cytosolic aldehyde dehydrogenase which comprises growing the host cells of the host vector system under suitable conditions permitting production of the polypeptide and recovering the polypeptide so produced.

In addition, this invention provides a method of detecting expression of a glutamylcysteine synthetase in a cell which comprises obtaining total mRNA from the cell, contacting the mRNA so obtained with a labelled nucleic acid molecule of the isolated mammalian nucleic acid molecule encoding an cytosolic aldehyde dehydrogenase under hybridizing conditions, determining the presence of mRNA hybridized to the molecule, and thereby detecting the expression of the cytosolic aldehyde dehydrogenase in the cell.

In addition, this invention provides a method of producing a polypeptide having the biological activity of a mammalian glutamylcysteine synthetase which comprises growing the host cells of the host vector system under suitable conditions permitting production of the polypeptide and recovering the polypeptide so produced.

In addition, this invention provides an antibody directed against an amino acid molecule a cytosolic aldehyde dehydrogenase.

In addition, this invention provides an antibody directed against an amino acid molecule a glutamylcysteine synthetase.

In addition, this invention provides an immunoassay for measuring the amount of a mammalian cytosolic aldehyde dehydrogenase in a biological sample comprising steps of: a) contacting the biological sample with at least one antibody, either monoclonal or ployclonal, to form a complex with said antibody and the cytosolic aldehyde dehydrogenase, and b) measuring the amount of the cytosolic aldehyde dehydrogenase in said biological sample by measuring the amount of said complex.

In addition, this invention provides a transgenic nonhuman mammal which comprises the isolated mammalian nucleic acid molecule encoding an cytosolic aldehyde dehydrogenase or a glutamylcysteine synthetase.

In addition, this invention provides a transgenic nonhuman mammal whose genome comprises antisense DNA complementary to DNA encoding a cytosolic aldehyde dehydrogenase so placed as to be transcribed into antisense mRNA complementary to mRNA encoding the cytosolic aldehyde dehydrogenase and which hybridizes to mRNA encoding the mammalian cytosolic aldehyde dehydrogenase thereby reducing its translation.

In addition, this invention provides a transgenic nonhuman mammal whose genome comprises antisense DNA complementary to DNA encoding a glutamylcysteine synthetase so placed as to be transcribed into antisense mRNA complementary to mRNA encoding the glutamylcysteine synthetase and which hybridizes to mRNA encoding the mammalian glutamylcyseine synthetase thereby reducing its translation.

In addition, this invention provides an immunoassay for measuring the amount of a mammalian glutamylcysteine synthetase in a biological sample comprising steps of: a) contacting the biological sample with at least one antibody, either monoclonal or polyclonal, to form a complex with said antibody and the glutamylcysteine synthetase, and b) measuring the amount of the glutamylcysteine synthetase in said biological sample by measuring the amount of said complex.

BRIEF DESCRIPTION OF FIGURES

FIG. 2 pLAldo-X Plasmid Construction.

FIG. 4 (Parts 1–7) Nucleotide sequence of the 1842 bp full-length Aldehyde dehydrogenase (Aldh-1) cDNA sequence (SEQ. ID. NO. 1). The translation initiation codon (ATG) is preceded by an in frame translation stop codon, tag (underlined).

FIG. 5 (Parts 1–5) Aldehyde dehydrogenase (Aldh-1) amino acid sequence (SEQ. ID. NO. 2).

FIG. 6 (Parts 1–9) Nucleotide sequence of the 2904 bp full length glutamylcysteine synthetase (γ-GCS) cDNA sequence (SEQ. ID. NO. 3). The translation initiation codon (ATG) is preceded by an in frame translation stop codon, tga (underlined).

FIG. 7 (Parts 1–6) Glutamylcysteine synthetase (γ-GCS) amino acid sequence (SEQ. ID. NO. 4).

DETAILED DESCRIPTION OF INVENTION

Figure 1:
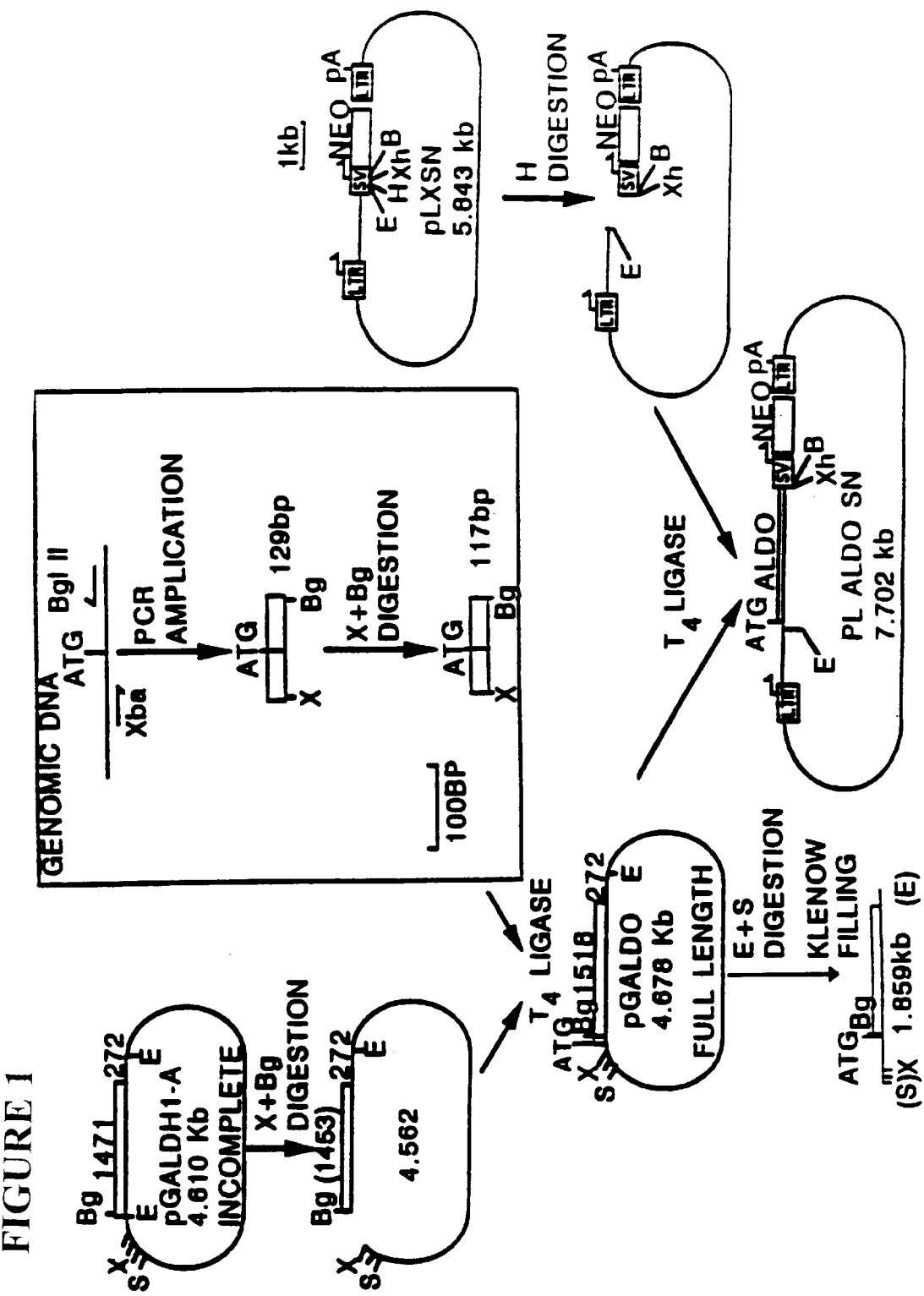
FIG. 1 pLAIdo-SN Plasmid Construction, where ALDH1=Human cytosolic aldehyde dehydrogenase 1, pG=pGEM, B=BamH1, Bg=BglII, S=SalI, E=EcoRI, X=XbaI, Xh=XhoI, H=HpaI.

Throughout this application, references to specific nucleotides are to nucleotides present on the coding strand of the nucleic acid. The following standard abbreviations are used throughout the specification to indicate specific nucleotides:

C=cytosine A=adenosine
T=thymidine G=guanosine

A "gene" means a nucleic acid molecule, the sequence of which includes all the information required for the normal regulated production of a particular protein, including the structural coding sequence, promoters and enhancers.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The DNA molecules described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

This invention provides a vector which comprises a nucleic acid molecule encoding a human cytosolic aldehyde dehydrogenase inserted into a site within a region of the vector which is not essential for its replication. The vector may be a viral vector. Further, the viral vector may be a double-stranded DNA viral vector.

In one embodiment, the above described nucleic acid molecules are RNA. In another embodiment, the nucleic acid molecules are DNA. In a further embodiment, the DNA molecules are genomic. In a still further embodiment, the DNA molecules are cDNAs. Further, the nucleic acid molecule encoding the cytosolic aldehyde dehydrogenase may be substantially the same sequence show in FIG. 4 (SEQ ID NO: 1).

In addition, this invention provides a retroviral vector, which comprises a nucleic acid molecule encoding a human cytosolic aldehyde dehydrogenase inserted into a site within a region of the vector which is not essential for its replication. The vector may be a retroviral vector. Further, the retroviral vector may be a double-stranded DNA retroviral vector.

A used in this invention, human cytosolic aldehyde dehydrogenase is used interchangeable with human aldehyde dehydrogenase 1. In addition, a human cytosolic aldehyde dehydrogenase means a full length human cytosolic aldehyde dehydrogenase.

This invention provides the above described retroviral vector, wherein the vector comprises DNA from a murine virus corresponding to two long terminal repeats, and a packaging signal. In an embodiment, the murine virus is Moloney murine leukemia virus. In another embodiment, the murine virus is Maloney murine sarcoma virus. In a further embodiment, the 3' long terminal repeat corresponds to that present in Maloney murine leukemia virus and the 5' long terminal repeat corresponds to that present in Maloney murine sarcoma virus.

Vectors include but are not limited to: adenovirus, simian virus 40 (SV40), cytomegalovirus (CMV), mouse mammary tumor virus (MMTV), Malony murine leukemia virus, murine sarcoma virus, and Rous sarcoma virus, DNA delivery systems, i.e liposomes, and expression plasmid delivery systems.

It is well known in the art that the packaging signal may contain splice donors and splice acceptors which are important for gene expression.

The retroviral vector may further comprise a DNA sequence corresponding to a second mammalian gene. The second mammalian gene is derived from mammalian cells and encodes a protein normally expressed in mammalian cells. The second mammalian gene may be a cDNA sequence operably linked to a promoter of DNA expression or a genomic DNA sequence. In one embodiment of this invention, the second mammalian gene is a gene encoding a non-selectable phenotype. As used herein, a "non-selectable phenotype" means the expression of a gene which cannot be selected for by any of the conventional means, i.e., with drugs, heat or other conventionally used selection pressures. A non-selectable phenotype means that systems containing a mixture of cells, some of which contain cells positive for the non-selectable phenotype and some of which are negative, cannot be manipulated by conventional means such that only cells positive for the non-selectable phenotype survive the manipulation. Genes encoding a non-selectable phenotype useful in accordance with the practice of this invention include insulin, β-globin and major histocompatibiltiy genes. However, the practice of this invention is not limited to the insertion of only these genes into the retroviral vector. Other mammalian genes suitable for inclusion in a retroviral vector and insertion into a mammalian cell are also encompassed by the practice of this invention.

The second mammalian gene will be packed by the retroviral packaging cell into retroviral particles by virtue of its inclusion in the retroviral vector. Selection of retroviral packaging cells capable of producing a sufficiently high titer of retroviral particles enables the cell to be used in a method of transducing a recipient cell with the gene of interest. (Banket et al. U.S. Pat. No. 5,278,056, issued Jan. 11, 1994.)

In addition, this invention provides a vector which comprises a nucleic acid molecule encoding a human glutamylcysteine synthetase inserted into a site within a region of the vector which is not essential for its replication. The vector may be a viral vector. Further, the viral vector may be a double-stranded DNA viral vector.

In one embodiment, the above described nucleic acid molecules are RNA. In another embodiment, the nucleic acid molecules are DNA. In a further embodiment, the DNA molecules are genomic. In a still further embodiment, the DNA molecules are cDNAs. Further, the nucleic acid molecule encoding the glutamylcysteine synthetase may be substantially the same sequence shown in FIG. 6 (SEQ ID NO: 3).

In addition, this invention provides a retroviral vector, which comprises a nucleic acid molecule encoding a human glutamylcysteine synthetase inserted into a site within a region of the vector which is not essential for its replication. The vector may be a retroviral vector. Further, the retroviral vector may be a double-stranded DNA retroviral vector.

In one embodiment, this invention provides a plasmid which comprises the double-stranded DNA retroviral vector which comprises cDNA encoding a human cytosolic aldehyde dehydrogenase inserted into a site within a region of the vector which is not essential for its replication.

In addition, this invention provides a plasmid which comprises the aldehyde dehydrogenase or glutamylcysteine synthetase viral vector or retroviral vector. In an embodiment, the plasmid is designated pLAldo-SN (ATCC Accession No. 69238). The plasmid pLAldo-SN was introduced into E. coli HB101 and deposited with the American Type Culture Collection (ATCC), 10801 University Boulevard, Manassas Va. 20110-2209, U.S.A. on Feb. 10, 1993 under the provisions of the Budapest Treaty for the International Recognition of the Deposit of Microorganism for the Purposes of Patent Procedure. The E. coli HB101 containing pLAldo-SN was accorded with ATCC Accession number 69238. In another embodiment, the plasmid is designated pLAldoX.

In addition, this invention provides, a plasmid designated pLGCS-X. The plasmid, pLGCS-X was introduced into E. coli DH5αand deposited with the American Type Culture Collection (ATCC), 10801 University Boulevard, Manassas Va. 20110-2209, U.S.A. on Mar. 24, 1994 under the provisions of the Budapest Treaty for the International Recognition of the Deposit of Microorganism for the Purposes of Patent Procedure.

This invention also provides a mammalian retroviral producer cell which comprises the double-stranded DNA retroviral vector having cDNA encoding a human cytosolic aldehyde dehydrogenase inserted into a site within a region of the vector which is not essential for its replication, the plasmid, pLAldo-SN or the plasmid, pLAldoX.

In one embodiment, pAldo-SN is introduced into the PA317 cell and the producer cell formed is designated, pLAldo-SN PA317cl.6. This cell line, pLAldo-SN PA317cl.6, was deposited with the American Type Culture Collection (ATCC), 10801 University Boulevard, Manassas Va., 20110-2209, U.S.A. on Feb. 10, 1993 under the provisions of the Budapest Treaty for the International Recognition of the Deposit of Microorganism for the Purposes of Patent Procedure. The PA317 cell containing pLAldo-SN was accorded with ATCC Accession number CRL 11265.

This invention also provides a human cell which comprises the double-stranded DNA retroviral vector which comprises cDNA encoding a human cytosolic aldehyde dehydrogenase inserted into a site within a region of the vector which is not essential for its replication, the plasmid, pLAldo-SN or the plasmid, pLAldo. In one embodiment, the human cell is a human hematopoietic cell. In another embodiment, the human cell is a bone marrow cell.

In addition, this invention provides a host vector system for the production of a polypeptide having the biological activity of a cytosolic aldehyde dehydrogenase which comprises a plasmid and a suitable host. The host vector system may be a bacterial cell, insect cell, viral cell or mammalian cell. The plasmid may be a pLALdo-SN or pLAldo as hereinabove discussed.

The nucleic acid molecule may be a DNA, RNA, cDNA. Further, the nucleic acid molecule encoding the human cytosolic aldehyde dehydrogenase may have substantially the same sequence shown in FIG. 4 (SEQ ID NO: 1).

Further, this invention provides a host vector system for the production of a polypeptide having the biological activity of an glutamylcysteine synthetase which comprises a plasmid and a suitable host.

In addition, this invention provides a method for introducing a selectable marker into a mammalian cell which comprises transfecting the cell with a nucleic acid molecule encoding human glutamylcysteine synthetase. The nucleic acid molecule may be a DNA, RNA or cDNA molecule.

The nucleic acid molecule amy be a DNA, RNA, cDNA. Further, the nucleic acid molecule encoding the human glutamylcysteine synthetase may have substantially the same sequence shown in FIG. 6 (SEQ ID NO: 3).

This invention provides a method for reducing the toxic effects of a cyclophosphamide in a subject which comprises replacing the subject's hematopoietic cells with hematopoietic cells which carries the cytosolic aldehyde dehydrogenase gene so as to reduce the toxic effects of the cyclophosphamide in the subject.

As used herein, a cyclophosphamide is cyclophosphamide or a derivative or homolog thereof which is effective as a cancer chemotherapeutic agent through the same mechanism or mode of action as cyclophosphamide. One example of such derivative is maphosphamide.

One method to produce hematopoietic cells which carries the cytosolic aldehyde dehydrogenase (Aldh1) is to introduce the double-stranded DNA retroviral vector which comprises cDNA encoding a human cytosolic aldehyde dehydrogenase inserted into a site within a region of the vector which is not essential for its replication into hematopoietic cells. The retroviral vector carrying the Aldh1 gene may be introduced to a packaging cell to generate a virus producing cell line. The viruses generated may then be used to infect hematopoietic cells. Other ways for introducing the ALDH1 gene well known to a person of ordinary skill in the art are included by this invention. One such method is electroporation and others including but are not limited to calcium phosphate precipitation technology, other viral vector systems such as adeno-associated virus system, lipofection and microinjection may be used in accordance with this invention.

This invention further provides a method for introducing a selectable marker into a mammalian cell which comprises transfecting the cell with DNA encoding human cytosolic aldehyde dehydrogenase.

In addition, this invention provides a method for selecting mammalian cells expressing protein of interest which comprises a) introducing into the cells a DNA molecule comprising DNA encoding the protein of interest and DNA encoding human cytosolic aldehyde dehydrogenase; b) culturing the resulting transfected cells; and c) selecting cells which express human cytosolic aldehyde dehydrogenase, so as to obtain cells which express the protein of interest. In an embodiment, the DNA molecule of step (a) of the above described method is part of a retroviral vector.

In addition, this invention provides a method for selecting mammalian cells expressing protein of interest which comprises: a). introducing into the cells a nucleic acid molecule comprising a nucleic acid molecule encoding the protein of interest and the nucleic acid molecule encoding human glutamylcysteine synthetase; b.) culturing the resulting transfected cells; and c.) selecting cells which express human glutamylcysteine synthetase, so as to obtain cells which express the protein of interest. The nucleic acid molecule may be a DNA, RNA or cDNA molecule.

The nucleic acid molecule amy be a DNA, RNA, cDNA. Further, the nucleic acid molecule encoding the human glutamylcysteine synthetase may have substantially the same sequence shown in FIG. 6 (SEQ ID NO: 3).

In addition, this invention provides an isolated mammalian nucleic acid molecule encoding a cytosolic aldehyde dehydrogenase. The isolated mammalian nucleic acid molecule may have substantially the same sequence shown in FIG. 4 (SEQ ID NO: 1). The isolated nucleic acid molecule may be a DNA, RNA, or cDNA. Further, the isolated nucleic acid molecule may be derived from a human.

In addition, this invention provides an isolated mammalian nucleic acid molecule encoding a glutamylcysteine synthetase. The isolated mammalian nucleic acid molecule may have substantially the same sequence shown in FIG. 4 (SEQ ID NO: 1). The isolated nucleic acid molecule may be a DNA, RNA, or cDNA. Further, the isolated nucleic acid molecule may be derived from a human.

In addition, this invention provides a nucleic acid molecule of at least 15 nucleotides capable of specifically hybridizing with a sequence of the nucleic acid molecule of the isolated mammalian nucleic acid molecule encoding a cytosolic aldehyde dehydrogenase or a glutamylcysteine synthetase. The nucleic acid molecule may be a DNA, RNA, or cDNA.

This nucleic acid molecule produced can either be DNA or RNA. As used herein, the phrase "specifically hybridizing" means the ability of a nucleic acid molecule to recognize a nucleic acid sequence complementary to its own and to form double-helical segments through hydrogen bonding between complementary base pairs.

Nucleic acid probe technology is well known to those skilled in the art who will readily appreciate that such probes may vary greatly in length and may be labeled with a detectable label, such as a radioisotope or fluorescent dye, to facilitate detection of the probe. DNA probe molecules may be produced by insertion of a DNA molecule which encode aldehyde dehydrogenase into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

In addition, this invention provides a method of detecting expression of an aldehyde dehydrogenase in a cell which comprises obtaining total mRNA from the cell, contacting the mRNA so obtained with a labelled nucleic acid molecule of the isolated mammalian nucleic acid molecule encoding an cytosolic aldehyde dehydrogenase under hybridizing conditions, determining the presence of mRNA hybridized to the molecule, and thereby detecting the expression of the cytosolic aldehyde dehydrogenase in the cell.

In addition, this invention provides a method of producing a polypeptide having the biological activity of a mammalian cytosolic aldehyde dehydrogenase which comprises growing the host cells of the host vector system under suitable conditions permitting production of the polypeptide and recovering the polypeptide so produced.

In addition, this invention provides a method of detecting expression of a glutamylcysteine synthetase in a cell which comprises obtaining total mRNA from the cell, contacting the mRNA so obtained with a labelled nucleic acid molecule of the isolated mammalian nucleic acid molecule encoding an glutamylcysteine synthetase under hybridizing conditions, determining the presence of mRNA hybridized to the molecule, and thereby detecting the expression of the glutamylcysteine synthetase in the cell.

In addition, this invention provides a method of producing a polypeptide having the biological activity of a mammalian glutamylcysteine synthetase which comprises growing the host cells of the host vector system under suitable conditions permitting production of the polypeptide and recovering the polypeptide so produced.

Numerous mammalian cells may be used as hosts, including, but not limited to, the mouse fibroblast cell NIH 3T3, CHO cells, HeLa cells, Ltk⁻ cells, Cos cells, etc. Expression plasmids such as that described supra may be used to transfect mammalian cells by methods well known in the art such as calcium phosphate precipitation, electroporation or DNA encoding the mammalian aldehyde dehydrogenase may be otherwise introduced into mammalian cells, e.g., by microinjection, to obtain mammalian cells which comprise DNA, e.g., cDNA or a plasmid, encoding a mammalian aldhehyde dehydrogenase.

In addition, this invention provides an antibody directed against the amino acid molecule a cytosolic aldehyde dehydrogenase. The amino acid sequence may be substantially the same as shown in FIG. 5 (SEQ ID NO: 2). The antibody may be a monoclonal or a polyclonal antibody.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of mammalian aldehyde dyhydrogenase in living animals, in humans, or in biological tissues or fluids isolated from animals or humans.

In addition, this invention provides an antibody directed against the amino acid molecule an glutamylcysteine synthetase. The amino acid sequence may be substantially the same as shown in FIG. 7 (SEQ ID NO: 4). The antibody may be a monoclonal or a polyclonal antibody.

In addition, this invention provides an immunoassay for measuring the amount of a mammalian cytosolic aldehyde dehydrogenase in a biological sample comprising steps of: a) contacting the biological sample with at least one antibody, either monoclonal or ployclonal, to form a complex with said antibody and the cytosolic aldehyde dehydrogenase, and b) measuring the amount of the cytosolic aldehyde dehydrogenase in said biological sample by measuring the amount of said complex.

In addition, this invention provides a transgenic nonhuman mammal which comprises the isolated mammalian nucleic acid molecule encoding an cytosolic aldehyde dehydrogenase.

In addition, this invention provides a transgenic nonhuman mammal whose genome comprises antisense DNA complementary to DNA encoding a cytosolic aldehyde dehydrogenase so placed as to be transcribed into antisense mRNA complementary to mRNA encoding the cytosolic aldehyde dehydrogenase and which hybridizes to mRNA encoding the mammalian cytosolic aldehyde dehydrogenase thereby reducing its translation. Further, the isolated nucleic acid molecule encoding the human cytosolic aldehyde dehydrogenase may have substantially the same sequence shown in FIG. 4 (SEQ ID NO: 1).

In addition, this invention provides an immunoassay for measuring the amount of a mammalian glutamylcysteine synthetase in a biological sample comprising steps of: a) contacting the biological sample with at least one antibody, either monoclonal or ployclonal, to form a complex with said antibody and the glutamylcysteine synthetase, and b) measuring the amount of the glutamylcysteine synthetase in said biological sample by measuring the amount of said complex.

In addition, this invention provides a transgenic nonhuman mammal which comprises the isolated mammalian nucleic acid molecule encoding a glutamylcysteine synthetase.

In addition, this invention provides a transgenic nonhuman mammal whose genome comprises antisense DNA complementary to DNA encoding a glutamylcysteine synthetase so placed as to be transcribed into antisense mRNA complementary to mRNA encoding the glutamylcysteine synthetase and which hybridizes to mRNA encoding the mammalian glutamylcysteine synthetase thereby reducing its translation. Further, the isolated nucleic acid molecule encoding the human cytosolic aldehyde dehydrogenase may have substantially the same sequence shown in FIG. 6 (SEQ ID NO: 3).

One aim of this invention is as follows: Chemotherapy with specific anticancer drugs represents a broadly used and very effective treatment modality for a variety of human cancers. However, most chemotherapeutic treatments have side-effects that severely limit their efficacy and cause risks in their usage. In particular, chemotherapy-induced cytopenia, i.e. the suppression of normal hematopoiesis (myelosuppression) leading to decreased production of leukocytes and platelets, represents a major factor of morbidity, mortality and underdosing in cancer treatment. It is conceivable that the ability to eliminate chemotherapy-induced cytopenia will lead both to decreased risk in cancer chemotherapy and, most notably, to the possibility of higher-dose treatment leading to higher cure rates.

This invention aims at solving the problem of cytopenia induced by the widely used chemotherapeutic drug cyclophosphamide (CP) and its analogs. CP is an anticancer drug with marked activity on a wide range of human tumors. Its activity is dose-dependent with a steep dose-response relationship and its dose-limiting toxicity is myelosuppression. Currently available strategies for treating CP-induced cytopenia are indirect and mainly based on accelerating the recovery of depressed hematopoiesis by using specific growth factors capable of stimulating bone marrow regeneration. The proposed invention is aimed at directly overcoming cyclophosphamide-induced cytopenia by rendering the hematopoietic cells resistant to the toxic effects of the drug.

One strategy of this invention is to make hematopoietic cells resistant to cyclophosphamide (CP) and its analogs by the introduction and expression of a gene whose protein product can metabolize CP into non-toxic and inactive compounds. Several lines of investigations have suggested that aldehyde dehydrogenase (Aldh) is involved in CP metabolism and resistance: i) cytotoxic metabolites of CP are generated via an aldehyde-containing intermediate that can be inactivated by Aldh (Struck et al., 1975; Colvin et al., 1976; Cox et al., 1975; Hill et al., 1972); ii) a correlation has been repeatedly observed between the levels of Aldh activity and the ability of various cell lines to resist to the CP toxicity (Cox et al., 1975; Hilton, 1984; Lin et al., 1988; iii) inhibitors of Aldh activity increase the sensitivity to CP toxicity (Sladek and Landkamer, 1985; Kohn and Sladek, 1987; Sahovic et al., 1988). In addition, it has been demonstrated that while the most immature hematopoietic cells express Aldh1, this activity is progressively downregulated in their functionally mature progeny including leukocytes, platelets and erythrocytes (Kastan et al., 1990), correlating with their sensitivity to CP. Thus, the stable expression of Aldh1 in hematopoietic precursors should make them and their progeny resistant to CP.

Based on these observations, a retroviral vector has been designed which carries and can express the human Aldh-1 gene. Retroviral vectors can transduce genes into human hematopoietic precursors (Bregni et al., 1992) which are used for bone marrow repopulation by autologous bone transplantation after chemotherapeutic treatment (Gianni et al., 1989).

One objective of this invention is to construct a retroviral vector capable of conferring resistance to the anti-cancer drug cyclophosphamide. This will be done by using the human aldehyde dehydrogenase gene which has been shown to confer resistance to cyclophosphamide and its anti-cancer analogs. A full-length cDNA for human Aldh1 is now isolated and used to construct a first vector which is shown to be capable of transducing the specific drug resistance phenotype to a variety of target cells including human CD34+ cells in vitro (FIG. 4, SEQ ID NO:1) (See Experimental Details I).

Chemotherapeutic Agents, include but are not limited to: Alkylating Agents, i.e. Nitrogen Mustards, Ethylenimines and Methylemelamines, Alkyl Sulfonates, Nitrosoureas, and Triazenes. Further chemotherapeutic agents include antimetabolites, i.e. Folic Acid Analogs, Pyrimidine Analogs, Purine Analogs and Related Inhibitors.

Further chemotherapeutic agents include natural products, i.e. Vinca Alkaloids, Epipodophyllotoxins, Antibiotics, Enzymes, Biological Response Modifiers. Further, chemotherapeutic agents include miscellaneous Agents, i.e. Plantinum Coordination Complexes, Anthracenedione, Substituted Urea, Methyl Hydrazine Derivative, and Adrenocortical Suppressant. Lastly, chemotherapeutic agents include hormones and antagonists, i.e. Adrenocorticosteroids, Progestins, Estrogens, Antiestrogen, Androgens, Antiandrogen, and Gonadotropin-releasing hormone analog.

In addition to its use in anti-cancer therapeutic protocols, a number of observations suggest that the ALDH gene can be used as a general selectable marker to select transduced cells both in vivo and in vitro using CP as a selection agent: i) CP exhibits marked cytotoxic activity on a wide range of eukaryotic cells in vitro; ii) the emergence of drug resistance to alkylating agents is a relatively rare and late event particularly in vitro; iii) CP kills sensitive cells after short exposure and the effect becomes evident within a very short time. Therefore, retroviral vectors carrying the Aldh gene and a second relevant gene to be expressed can be used for the selection of transduced cells in vitro as well as for the selection of transduced cells from a variety of tissue targets in vivo. This latter application is likely to be useful in the context of a variety of gene therapy protocols whenever a strong and continued selection of the transduced cells is necessary. The fact the CP is an already approved drug in humans represent an additional advantage of this strategy.

The Aldh1 gene can serve as a dominant selectable marker to permit both the in vitro and in vivo selection of cells transformed with a second gene of interest. The need for a selectable marker gene in gene transfer experiments stems from the usually low transfer efficiency and the high frequency of mutations and rearrangements leading to rapid functional inactivation of transduced gene. A selectable marker gene thus provides the means for expanding the usually small proportion of cells that have incorporated the gene of interest and are capable of expressing it in a functional form over time. The development of a selection system applicable to as wide a range of target cells as possible has become a central goal of gene transfer research, as clearly indicated by the substantial and growing number of different proposals.

The Aldh1 gene promises to represent an invaluable dominant selectable marker after co-transduction with an unrelated, unselectable gene of interest into cyclophosphamide-sensitive cells. To correct a genetic disease like ADA deficiency or β-thalassemia, it is essential to develop a strategy for the preferential in vivo expansion of the small number of hematopoietic stem cells that can be transduced with the relevant defective gene (i.e., the ADA or β-globin genes, with or without regulatory sequences). In fact, even an hypothetical 100% transduction efficiency of the small number of harvested stem cells used for in vitro manipulation experiments would represent a minor fraction of the overall pool of resident stem cells, left unchanged in the host bone marrow. To favor the engraftment of transduced cells by destroying the recipient bone marrow with ionizing radiations and/or myeloablative drugs is least acceptable in non-neoplastic diseases like ADA deficiency and β-thalassemia. Cyclophosphamide is an alkylating agent widely employed also in non-neoplastic diseases (i.e. autoimmune diseases) and its use according to standard doses and schedules is safe and devoid of major acute and chronic toxicities. Its short term administration over a number of courses to patients autografted with bone marrow cells transduced with a vector containing both ADA and ALDH genes is thus expected to confer a selective advantage to the infected cells, allowing their preferential in vivo expansion. The same principle applies to different models of gene therapy in which the target cell is cyclophosphamide-sensitive (i.e. T-lymphocytes, tumor cells, etc.) (for a review, see W. F. Anderson, 1992).

Aldh1 gene may be used as selectable marker to introduce human glutamylcysteine synthetase glue to generate cell capable of conferring resistance to anti-cancer alkylating agent such as cis-platinum, melphalan, ionizing radiations. The expression of human gamma-glutamylcysteine synthetase gene (γ-GCS) has been shown to correlate with the acquisition of resistance to alkylating in a variety of tumor cell lines in vitro. Aldh gene may be used as a selectable marker to facilitate the introduction of the γ-GCS genes into cells.

Another example is to generate cells which is capable of conferring resistance to human immunodeficiency virus (HIV) infection. DNA sequences coding dominant negative products or anti-sense RNAs capable of interfering at various levels with HIV infection may be introduced into $CD34^+$ cells using Aldh1 gene as selectable marker. The introduction of these DNA sequences should constitute an HIV-resistant T cell compartment in vivo.

One method to use Aldh1 gene as selectable marker includes inserting the Aldh1 gene and at least one gene of interest into a retroviral vector. The retroviral vector carrying the Aldh gene and the gene of interest may be introduced to a packaging cell to generate a virus producing cell line. The viruses generated may then be used to infect cell. Other ways of introducing a selectable marker into cells known in the art are included by this invention. One such method is electroporation and others including but are not limited to calcium phosphate precipitation technology, other viral vector systems such as adeno-associated virus system, lipofection and microinjection may be used in accordance with this invention.

To summarize, a retorviral vector carrying the Aldh1 gene can be used: i) to confer CP resistance to hematopoietic cells and their progeny allowing for treatment with high-dose CP in anti-cancer therapeutic regimens; ii) to use CP-resistance as a general marker for the selection of retrovirally transduced cells in vitro or in vivo.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

I. Construction of Retroviral Vector Which Carries the Aldehyde Dehydrogenase Gene A. pLAldo-Sn Plasmid Construction (FIG. 1)
1) Cloning of human cytosolic aldehyde dehydrogenase (Aldh1) full length cDNA A human liver cDNA library from Clonentech (HL1115A) was screened with a partial cDNA probe, kindly donated by L. C. Hsu (Hsu, L., et al., 1985). The probe, named Aldh1, corresponds to 1020 bp coding and 540 bp 3' flanking sequences.

A partial cDNA clone, pGA1dh1-A, was isolated with 1471 bp of coding sequences and 272 bp 3' flanking which lack 46 bp to the ATG.

In order to obtain the remaining 5' sequences, a PCR amplification on genomic DNA was achieved using a 5' end primer designed on the genomic sequence (Hsu, et al., 1989) and a 3' end primer based on the available sequence. The primers contain Xba I and Bgl II sites for cloning purposes. The PCR product, after Xba I and Bgl II digestion, was subcloned into pGA1dh1-A leading to plasmid containing the full length cDNA, pGA1do, of 1518 bp coding sequences, in which the natural Bgl II site 5' to PGA1DH1-A and 3' to the genomic PCR product are used to conserve the reading frame.

2) Construction of a retroviral vector plasmid carrying the human cytosolic aldehyde dehydrogenase gene.

The human cytosolic aldehyde dehydrogenase full length cDNA Aldo, (FIG. 6, SEQ ID NO: 1), derived from Eco RI and Sal I digestion of pGA1do and filling of the 3' recessive ends was subcloned into Hpa I of pLXSN, an amphotropic retroviral vector kindly donated by D. Miller (Miller, D., and Rosman, G., 1989) to generate pLAldo-SN.

B. pLAldoX Plasmid Construction (FIG. 2)

The human cytosolic aldehyde dehydrogenase full length cDNA, Aldo, derived from Eco RI and Sal I digestion of pGA1do and filling of the 3' recessive ends were subcloned into the pLNSX vector containing a neomycin gene, obtained from Dr. Miller (Miller, D., and Rosman, G., 1989). The derived plasmid contains 6,137 base pairs. The neomycin gene was cut out by BclI digestion. The digested vector was then filled-in, further digested with StuI, treated with calf-intestinal phosphatase (CIP) and LMP-purified. This digested vector was then ligated with the previously purified pAldo fragment containing the Aldehyde Dehydrogenase-1 Gene. The Aldehyde Dehydrogenase-1 gene was placed downstream of the vector's 5' LTR and the plasmid so formed is called pLAldoX which is 6,495 basepair long.

C. Generation of the Retrovirus

In order to generate an amphotropic retroviral vector carrying Aldo, the plasmid pLAldo-SN was transfected into the Ψ2 ecotropic packaging cell line (obtained from Mulligan, R. (Mann, et al., (1983) Cell 33:153–159) by the CaPO4 precipitation procedure. After 48 hours the supernatant of the transfected cell line which contained the ecotropic Aldo-SN virus was used to infect the amphotropic packaging cell line PA317 (obtained from ATCC CRL 9078) (Miller, D., and Buttimore, C., (1986) Mol. Cell. Biol. 6:2895). The infected cells were selected in neomycin containing medium and 30 clones were isolated for further characterization for virus titer and Aldh1 RNA expression. pLAldo-SN PA317 cl.6, 22 and 3 were shown to have the highest titer and Aldh1 RNA expression.

The above experiment was done using the plasmid, pLAldo-SN. Retroviruses may also be generated similarly using the plasmid pLAldoX.

II. Demonstration of Maphosphamide-resistance in pLAldo-SN Transduced Cells

1) Infection of K562 cells.

Figure 3:
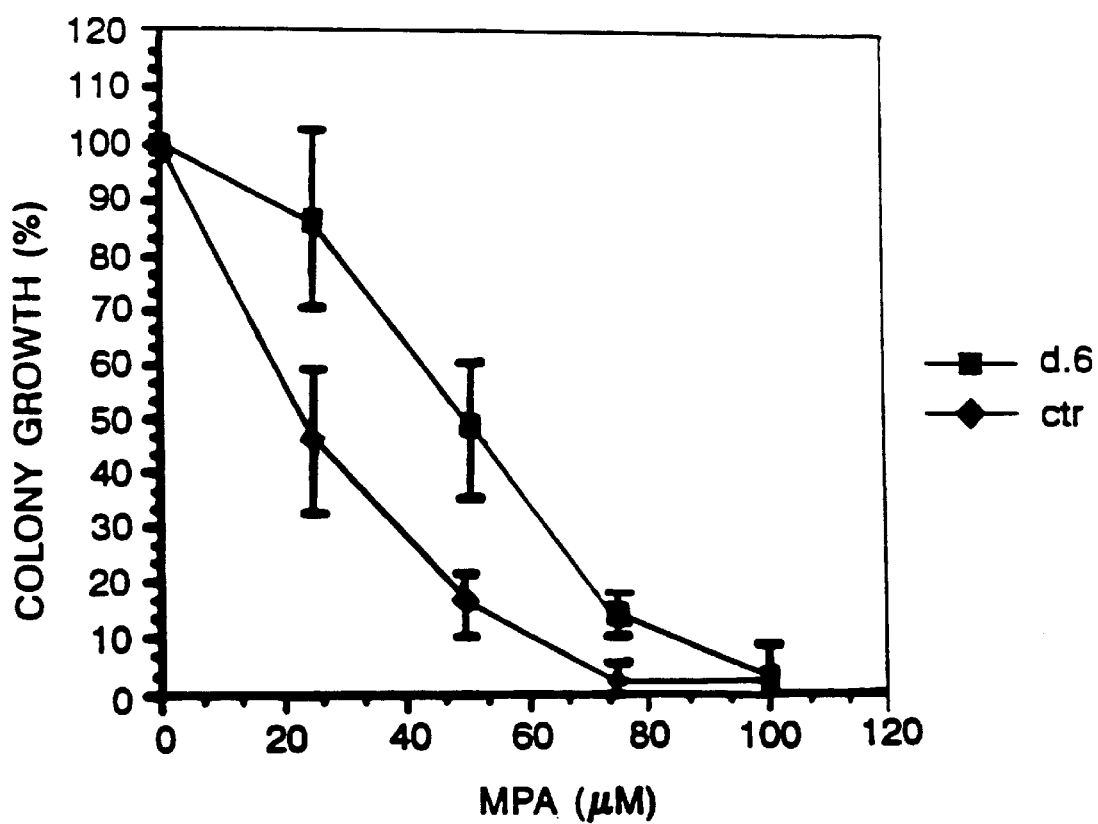
FIG. 3 Maphosphamide-resistance of pLAldo-SN transduced K562 cells (Lozzio and Lozzio, 1975). MPA is maphosphamide. The graph represents the mean value of three different experiments±standard deviations.

Virus-containing supernatant from pLAldo-SN PA317 cl.6 cells was used to infect K562 cell, a human pluripotent leukemic cell line. Wild type (ctr) and pLAldo-SN infected K562 cells were exposed to different concentrations of maphosphamide (MPA) for 30 minutes at 37° C. at $1\times10^6$ cells/ml and then plated at $3-5\times10^3$ cells/plate in 0.3% agar in 35 mm plates. MPA-resistance was scored as % of the colonies growing from MPA-selected vs unselected cells after 12 days of incubation at 37° C. and 5% $CO_2$. The graph in FIG. 3 represents the mean value of three different experiments±standard deviations. The results indicate that pLAldo-SN transduced K562 cells display increased resistance to MPA at concentrations ranging from 20 to 80 $\mu$M.

2) Infection of normal human hematopoietic progenitor cells.

Human hematopoietic progenitor cells, obtained by leukapheresis followed by ficoll-hypaque centrifugation, were preincubated for two days in Iscove Modified Dulbecco Medium (IMDM)+20% FDC+IL3+IL6 and then infected with different supernatants from PA317-pLAldo-SN clones. Cells were then exposed for 30 minutes at 37° C. to 5 $\mu$M of maphosphamide (MPA) at $1\times10^6$ cells/ml and plated in 60 wells of a 96 multiwell plates at 100 cells/well in IMDM+20% FCS+5637 CM 10% (bladder carcinoma conditioned media)+IL3+IL6+GM-CSF+idrocortisone $10^{-6}$M. MPA-resistance was scored as number of positive wells growing after 12 days of incubation at 37° C. and 5% CO2.

The results, showed in the following Table 1 indicate that three different LAldo-SN viral clones (originated from the corresponding PA317-pLAldo-SN cell clones) were able to confer MPA-resistance scored as the number of cells capable of growing after MPA treatment.

TABLE 1

Maphosphamide-resistance of pLAldo-SN-transduced human hematopoietic progenitor cells

| Samples | Number of positive wells | | MPA resistance % wells |
|---|---|---|---|
| | − MPA | + MPA | |
| Control | 58 | 5 | 8.6 |
| cl.22-infected | 60 | 15 | 25 |
| cl.6-infected | 60 | 20 | 33 |
| cl.3-infected | 60 | 41 | 68 |

III. Uses of the Human Cytosolic Aldehyde Dehydrogenase Gene as Selectable Marker In Vivo Construction of a retroviral vector carrying the human cytosolic aldehyde dehydrogenase gene and the human glucocerebrosidase (GCase) gene.

Aldo-GCase retroviral vector can be generated from the NTG plasmid (Correll, 1989) by removing the neo selectable marker and by inserting the coding sequence for the human cytosolic aldehyde dehydrogenase gene.

Human hematopoietic progenitor cells can be obtained by leukapheresis from a Gaucher disease patient treated with r-hu-IL3 (7 days at 5 g/kg/day continuous iv induction) following by either rhGM-CSF or rhG-CSF for 3–5 additional days (both at 5 g/kg/day). Daily leukaphereses can be repeated until $3 \times 10^9$ CD34+ cells (Siena et al., 1991) are harvested.

Light-density cells from each leukapheresis are obtained by Ficol-Hypaque centrifugation and infected with clinical-grade supernatant from PA317 clones producing high-titer Aldo-GCase vector free of helper virus.

Following infection, aliquots from each leukapheresis can be exposed for 30 minutes at 37° C. to 5 $\mu$M MPA and plated as described above. Twelve days later, MPA resistance are scored to assess the efficiency of transduction.

The bulk of infected cells can be washed by centrifugation and immediately reinfused without freezing. In vivo treatment with cyclophosphamide starts only 12 days later, following assessment of the proportion of MPA-resistant clones. Only in case of infection efficiency 30% (Bregni, et al., 1992) the patient can be treated with cyclophosphamide.

Two different selection protocols are sequentially tested. According to the first protocol, cyclophosphamide can be given at 100 mg/m2 per day for 14 consecutive days, as per standard schedules adopted in combination chemotherapy (Canellos et al., 1976). Before treatment, a bone marrow aspirate can be obtained to determine baseline frequency of Aldo-GCase infected and MPA-resistant clones. Bone marrow aspirate is repeated at the end of treatment and results compared with baseline data. If no or minor changes in the proportion of transfected cells are observed, and cells carrying the Aldo-GCase gene are identified, a different protocol using high-dose cyclophosphamide can be tested. Five to seven g/m2 cyclophosphamide are infused following by reGM-CSF or rhG-CSF administration (Gianni et al., 1990). The infusions can last longer than described (24 instead of 12 hours) to prevent cyclophosphamide concentration from rising about 5 $\mu$M. The expansion of MPA-positive bone marrow colonies are assessed before and after cyclophosphamide treatment by both PCR and MPA-resistance.

Figure 8:
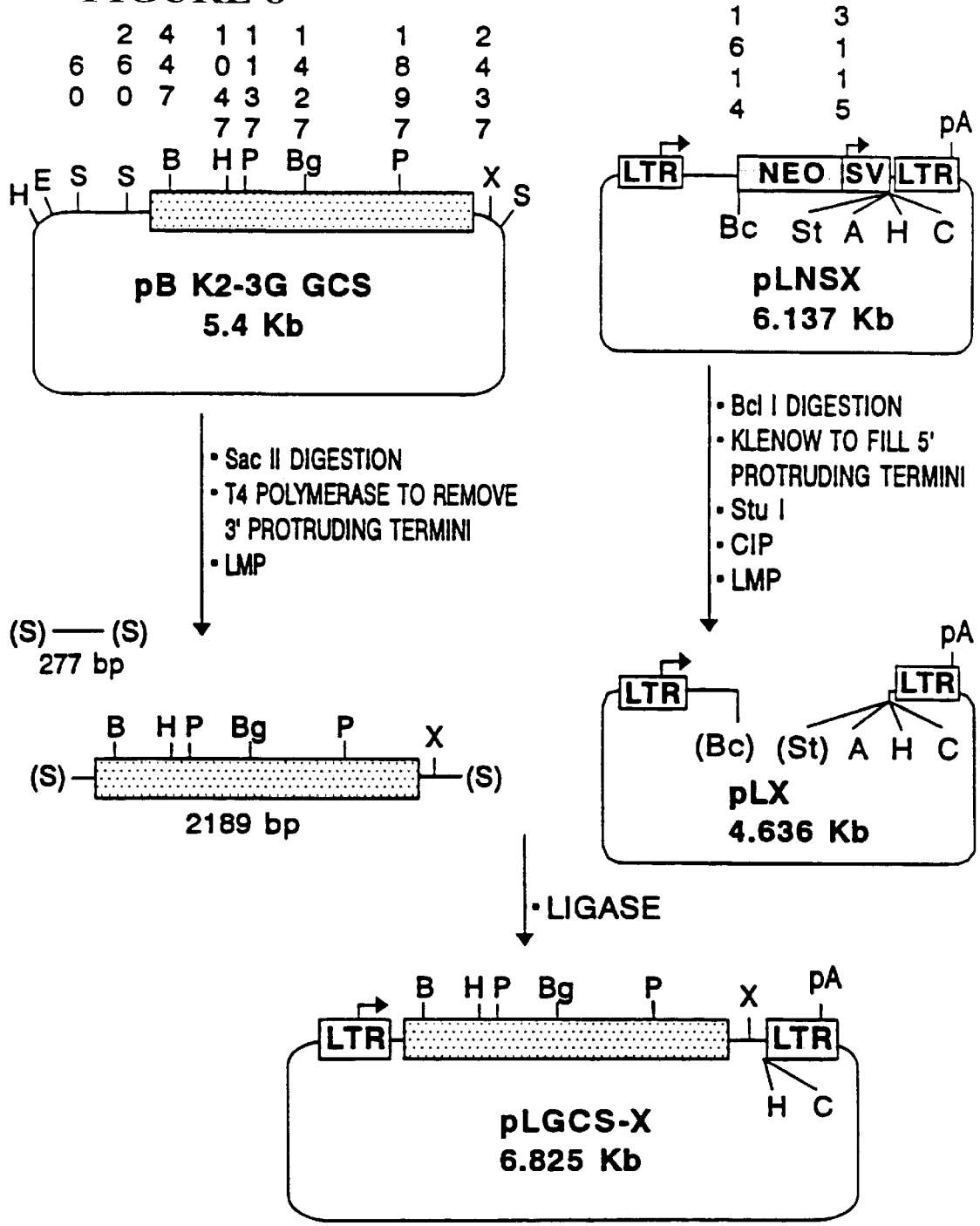
FIG. 8 pLGCS-X Plasmid Construction.

IV. Construction of Retroviral Vector Which Carries the Glutamylcysteine Synthetase Gene A. pLGCS-X Plasmid Construction (FIG. 8)

In order to obtain a full-length γ-GCS cDNA, a human kidney cDNA library (Clonentech, HL 1123) was screened with a partial γ-GCS cDNA probe (Pst I fragment, nucleotides 1137–1897 in the sequence shown in FIG. 2) obtained from R. T. Mulcahy. The inserts of two overlapping cDNA clones together spanning 2904 bp. of cDNA sequence were ligated using an internal Hind III site (position 1047) to generate the plasmid pB K2-3G GCS (FIG. 8). This plasmid was then digested with Sac I, the 3' protruding ends were filled using T4 polymerase and the insert was isolated by preparative electrophoresis in low melting point (LMP in FIG. 3) agarose. The fragment as then ligated using T4 ligase to the blunt ends of the pLX vector (obtained by BclI digestion, 5' protruding fill-in by Klenow fragment polymerase, StuI digestion, and dephosphorylation by calf intestine phosphatase) to generate the pLGCS-X vector.

REFERENCES

Anderson, W. F., (1992) 256:808.
Bregni, M, Magni, M., Siena, S., Di Nicola, M., Bonadonna, G., Gianni, A. M., (1992) Blood, 80:1418.
Canellos, et al (1976) Cancer 38:1882.
Colvin, M., Brundrett, R. B., Kan, M-N. N., Jardine, I., and Fenselau, C., (1976) Cancer Res., 36:1121.
Correll, (1989) PNAS, 86:8912.
Cox, P. J., Phillips, B. J., and Thomas, P., (1975) Cancer Res., 35:3755.
Eglitis (1991) Human Gene Ther. 2:195.
Gianni, A. M., Siena, S., Bregni, M., Tarella, C., Stern, A. C., Pileri, A., and Bonadonna, G., (1989) Lancet, 2:580.
Gianni, et al., (1990) J. Clin. Oncol. 8:768.
Hill, D. L., Laster, W. R., Jr., and Stuck, R. F., (1972) Cancer Res., 32:658.
Hilton, J., (1984) Cancer Res., 44:5156.
Hsu, L. D., et al., (1985) Proc. Natl. Acad. Sci., 82:3771–3775.
Hsu, L. C., et al., (1989) Genomics, 5:857–865.
Kastan, M. B., Schlaffer, E., Russo, J. M., Colvin, O. M., Civin, C. I., and Hilton, J., (1990) Blood, 75:1947.
Khon, et al., (1987) Biochem. Pharmacol., 36:2805.
Lin, K-h, Brennam, M. D., and Lindahl, R., (1988) Cancer Res., 48:7009.
Mann, R. et al., (1983) Cell 33:153.
Miller, D. and Rosman, G., (1989) Biotechniques 7:980–990.2.
Miller, D. and Buttimore, C. (1986) Mol. Cell. Biol. 6: 2895.
Lozzio and Lozzio, (1975) Blood 45:321.
Sahovic, E. A., Colvin, M., Hilton, J., and Ogawa, M., (1988) Cancer Res., 48:1223.
Sladek, N. E., and Landhamer, G. J., (1985) Cancer Res., 45:1549.
Struck, R. P., Kirk, M. C., Wiu, M. H., and Laster, W. H., Jr., (1975) Biomed. Mass Spestrom., 2:46.

What is claimed is:

1. A retroviral vector which comprises a cDNA encoding a human cytosolic aldehyde dehydrogenase having the sequence shown in FIG. 5 (SEQ ID NO: 2).

2. The plasmid designated pLAldo-SN (ATCC Accession No. 69238).

3. A mammalian retroviral producer cell which comprises the retroviral vector of claim 1 or the plasmid of claim 2.

4. A producer cell which comprises the plasmid of claim 2 designated pLAldo-SN PA317.cl.6 (ATCC Accession No. CRL 11265).

5. A human cell which comprises the retroviral vector of claim 1 or the plasmid of claim 2.

6. The human cell of claim 5, wherein said cell is a hematopoietic cell.

7. The hematopoietic cell of claim 6, wherein said cell is a bone marrow cell.

8. A host vector system for the production of a polypeptide having the biological activity of a cytosolic aldehyde dehydrogenase which comprises the plasmid of claim 2 and a suitable host.

9. The host vector system of claim 8, wherein the suitable host is a bacterial cell, insect cell, or mammalian cell.

10. A method of producing a polypeptide having the biological activity of a human cytosolic aldehyde dehydrogenase which comprises growing the host vector system of claim 8 under suitable conditions permitting production of the polypeptide and recovering the polypeptide so produced.

11. An isolated cDNA encoding a human cytosolic aldehyde dehydrogenase having the amino acid sequence shown in FIG. 5 (SEQ ID NO: 2).

12. The isolated cDNA of claim 11 wherein the cDNA molecule has the nucleotide sequence shown in FIG. 4 (SEQ ID NO:1).

13. An isolated nucleic acid molecule encoding a human cytosolic aldehyde dehydrogenase having the amino acid sequence shown in FIG. 5 (SEQ ID NO: 2), wherein the nucleic acid molecule is an RNA molecule.

14. A method of detecting expression of an aldehyde dehydrogenase in a cell which comprises obtaining total mRNA from the cell, contacting the mRNA so obtained with a labelled nucleic acid molecule of claim 13 under hybridizing conditions, determining the presence of mRNA hybridized to the molecule, and thereby detecting the expression of the cytosolic aldehyde dehydrogenase in the cell.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1842 base pairs
      (B) TYPE: nucleic acid
      (C) STRANDEDNESS: single
      (D) TOPOLOGY: linear (ii) MOLECULE TYPE: cDNA (iii) HYPOTHETICAL: N (iv) ANTI-SENSE: N (v) FRAGMENT TYPE: N-terminal (ix) FEATURE:
      (A) NAME/KEY: CDS
      (B) LOCATION: 2..1568

(xi) SEQUENCE DESCRIPTION: SEQ ID NO:1:

```
C TAG AAC CAA ATT GCT GAG CCA GTC ACC TGT GTT CCA GGA GCC GAA         46
  .  Asn Gln Ile Ala Glu Pro Val Thr Cys Val Pro Gly Ala Glu
     1               5                  10                  15

TCA GAA ATG TCA TCC TCA GGC ACG CCA GAC TTA CCT GTC CTA CTC ACC       94
Ser Glu Met Ser Ser Ser Gly Thr Pro Asp Leu Pro Val Leu Leu Thr
                20                  25                  30

GAT TTG AAG ATT CAA TAT ACT AAG ATC TTC ATA AAC AAT GAA TGG CAT      142
Asp Leu Lys Ile Gln Tyr Thr Lys Ile Phe Ile Asn Asn Glu Trp His
            35                  40                  45

GAT TCA GTG AGT GGC AAG AAA TTT CCT GTC TTT AAT CCT GCA ACT GAG      190
Asp Ser Val Ser Gly Lys Lys Phe Pro Val Phe Asn Pro Ala Thr Glu
        50                  55                  60

GAG GAG CTC TGC CAG GTA GAA GAA GGA GAT AAG GAG GAT GTT GAC AAG      238
Glu Glu Leu Cys Gln Val Glu Glu Gly Asp Lys Glu Asp Val Asp Lys
    65                  70                  75

GCA GTG AAG GCC GCA AGA CAG GCT TTT CAG ATT GGA TCT CCG TGG CGT      286
Ala Val Lys Ala Ala Arg Gln Ala Phe Gln Ile Gly Ser Pro Trp Arg
80                  85                  90                  95

ACT ATG GAT GCT TCC GAG AGG GGG CGA CTA TTA TAC AAG TTG GCT GAT      334
Thr Met Asp Ala Ser Glu Arg Gly Arg Leu Leu Tyr Lys Leu Ala Asp
                100                 105                 110

TTA ATC GAA AGA GAT CGT CTG CTG GCG ACA ATG GAG TCA ATG GAG TCA      382
Leu Ile Glu Arg Asp Arg Leu Leu Ala Thr Met Glu Ser Met Glu Ser
            115                 120                 125

ATG AAT GGT GGA AAA CTC TAT TCC AAT GCA TAT CTG AAT GAT TTA GCA      430
Met Asn Gly Gly Lys Leu Tyr Ser Asn Ala Tyr Leu Asn Asp Leu Ala
        130                 135                 140

GGC TGC ATC AAA ACA TTG CGC TAC TGT GCA GGT TGG GCT GAC AAG ATC      478
Gly Cys Ile Lys Thr Leu Arg Tyr Cys Ala Gly Trp Ala Asp Lys Ile
    145                 150                 155

CAG GGC CAG GGC CGT ACA ATA CCA ATT GAT GGA AAT TTT TTT ACA TAT      526
Gln Gly Gln Gly Arg Thr Ile Pro Ile Asp Gly Asn Phe Phe Thr Tyr
160                 165                 170                 175

ACA AGA CAT GAA CCT ATT GGG GTA TGT GGC CAA ATC ATT CCT TGG AAT      574
Thr Arg His Glu Pro Ile Gly Val Cys Gly Gln Ile Ile Pro Trp Asn
                180                 185                 190

TTC CCG TTG GTT ATG CTC ATT TGG AAG ATA GGG CCT GCA CTG AGC TGT      622
```

```
                  Phe Pro Leu Val Met Leu Ile Trp Lys Ile Gly Pro Ala Leu Ser Cys
                                  195                 200                 205

GGA AAC ACA GTG GTT GTC AAA CCA GCA GAG CAA ACT CCT CTC ACT GCT                670
Gly Asn Thr Val Val Val Lys Pro Ala Glu Gln Thr Pro Leu Thr Ala
            210                 215                 220

CTC CAC GTG GCA TCT TTA ATA AAA GAG GCA GGG TTT CCT CCT GGA GTA                718
Leu His Val Ala Ser Leu Ile Lys Glu Ala Gly Phe Pro Pro Gly Val
        225                 230                 235

GTG AAT ATT GTT CCT GGT TAT GGG CCT ACA GCA GGG GCA GCC ATT TCT                766
Val Asn Ile Val Pro Gly Tyr Gly Pro Thr Ala Gly Ala Ala Ile Ser
240                 245                 250                 255

TCT CAC ATG GAT ATA GAC AAA GTA GCC TTC ACA GGA TCA ACA GAG GTT                814
Ser His Met Asp Ile Asp Lys Val Ala Phe Thr Gly Ser Thr Glu Val
                260                 265                 270

GGC AAG TTG ATC AAA GAA GCT GCC GGG AAA AGC AAT CTG AAG AGG GTG                862
Gly Lys Leu Ile Lys Glu Ala Ala Gly Lys Ser Asn Leu Lys Arg Val
            275                 280                 285

ACC CTG GAG CTT GGA GGA AAG AGC CCT TGC ATT GTG TTA GCT GAT GCC                910
Thr Leu Glu Leu Gly Gly Lys Ser Pro Cys Ile Val Leu Ala Asp Ala
        290                 295                 300

GAC TTG GAC AAT GCT GTT GAA TTT GCA CAC CAT GGG GTA TTC TAC CAC                958
Asp Leu Asp Asn Ala Val Glu Phe Ala His His Gly Val Phe Tyr His
305                 310                 315

CAG GGC CAG TGT TGT ATA GCC GCA TCC AGG ATT TTT GTG GAA GAA TCA               1006
Gln Gly Gln Cys Cys Ile Ala Ala Ser Arg Ile Phe Val Glu Glu Ser
320                 325                 330                 335

ATT TAT GAT GAG TTT GTT CGA AGG AGT GTT GAG CGG GCT AAG AAG TAT               1054
Ile Tyr Asp Glu Phe Val Arg Arg Ser Val Glu Arg Ala Lys Lys Tyr
                340                 345                 350

ATC CTT GGA AAT CCT CTG ACC CCA GGA GTC ACT CAA GGC CCT CAG ATT               1102
Ile Leu Gly Asn Pro Leu Thr Pro Gly Val Thr Gln Gly Pro Gln Ile
            355                 360                 365

GAC AAG GAA CAA TAT GAT AAA ATA CTT GAC CTC ATT GAG AGT GGG AAG               1150
Asp Lys Glu Gln Tyr Asp Lys Ile Leu Asp Leu Ile Glu Ser Gly Lys
        370                 375                 380

AAA GAA GGG GCC AAA CTG GAA TGT GGA GGA GGC CCG TGG GGG AAT AAA               1198
Lys Glu Gly Ala Lys Leu Glu Cys Gly Gly Gly Pro Trp Gly Asn Lys
385                 390                 395

GGC TAC TTT GTC CAG CCC ACA GTG TTC TCT AAT GTT ACA GAT GAG ATG               1246
Gly Tyr Phe Val Gln Pro Thr Val Phe Ser Asn Val Thr Asp Glu Met
400                 405                 410                 415

CGC ATT GCC AAA GAG GAG ATT TTT GGA CCA GTG CAG CAA ATC ATG AAG               1294
Arg Ile Ala Lys Glu Glu Ile Phe Gly Pro Val Gln Gln Ile Met Lys
                420                 425                 430

TTT AAA TCT TTA GAT GAC GTG ATC AAA AGA GCA AAC AAT ACT TTC TAT               1342
Phe Lys Ser Leu Asp Asp Val Ile Lys Arg Ala Asn Asn Thr Phe Tyr
            435                 440                 445

GGC TTA TCA GCA GGA GTG TTT ACC AAA GAC ATT GAT AAA GCC ATA ACA               1390
Gly Leu Ser Ala Gly Val Phe Thr Lys Asp Ile Asp Lys Ala Ile Thr
        450                 455                 460

ATC TCC TCT GCT CTG CAG GCA GGA ACA GTG TGG GTG AAT TGC TAT GGC               1438
Ile Ser Ser Ala Leu Gln Ala Gly Thr Val Trp Val Asn Cys Tyr Gly
465                 470                 475

GTG GTA AGT GCC CAG TGC CCC TTT GGT GGA TTC AAG ATG TCT GGA AAT               1486
Val Val Ser Ala Gln Cys Pro Phe Gly Gly Phe Lys Met Ser Gly Asn
480                 485                 490                 495

GGA AGA GAA CTG GGA GAG TAC GGT TTC CAT GAA TAT ACA GAG GTC AAA               1534
Gly Arg Glu Leu Gly Glu Tyr Gly Phe His Glu Tyr Thr Glu Val Lys
                500                 505                 510
```

```
ACA GTC ACA GTG AAA ATC TCT CAG AAG AAC TCA T AAAGAAAATA              1578
Thr Val Thr Val Lys Ile Ser Gln Lys Asn Ser
            515                 520

CAAGAGTGGA GAGAAGCTCT TCAATAGCTA AGCATCTCCT TACAGTCACT AATATAGTAG     1638

ATTTTAAAGA CAAAATTTTT CTTTTCTTGA TTTTTTTTAA ACATAAGCTA AATCATATTA     1698

GTATTAATAC TACCCATAGA AAACTTGACA TGTAGCTTCT TCTGAAAGAA TTATTTGCCT     1758

TCTGAAATGT GACCCCCAAG TCCTATCCTA AATAAAAAAA GACAAATTCG GATGTATGAT     1818

CTCTCTAGCT TTGTCATAGT TATG                                            1842

(2) INFORMATION FOR SEQ ID NO:2:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:2:

Asn Gln Ile Ala Glu Pro Val Thr Cys Val Pro Gly Ala Glu Ser Glu
1               5                   10                  15

Met Ser Ser Gly Thr Pro Asp Leu Pro Val Leu Leu Thr Asp Leu
            20                  25                  30

Lys Ile Gln Tyr Thr Lys Ile Phe Ile Asn Asn Glu Trp His Asp Ser
        35                  40                  45

Val Ser Gly Lys Lys Phe Pro Val Phe Asn Pro Ala Thr Glu Glu Glu
    50                  55                  60

Leu Cys Gln Val Glu Glu Gly Asp Lys Glu Asp Val Asp Lys Ala Val
65              70                  75                  80

Lys Ala Ala Arg Gln Ala Phe Gln Ile Gly Ser Pro Trp Arg Thr Met
                85                  90                  95

Asp Ala Ser Glu Arg Gly Arg Leu Leu Tyr Lys Leu Ala Asp Leu Ile
            100                 105                 110

Glu Arg Asp Arg Leu Leu Ala Thr Met Glu Ser Met Glu Ser Met Asn
        115                 120                 125

Gly Gly Lys Leu Tyr Ser Asn Ala Tyr Leu Asn Asp Leu Ala Gly Cys
130                 135                 140

Ile Lys Thr Leu Arg Tyr Cys Ala Gly Trp Ala Asp Lys Ile Gln Gly
145                 150                 155                 160

Gln Gly Arg Thr Ile Pro Ile Asp Gly Asn Phe Phe Thr Tyr Thr Arg
            165                 170                 175

His Glu Pro Ile Gly Val Cys Gly Gln Ile Ile Pro Trp Asn Phe Pro
        180                 185                 190

Leu Val Met Leu Ile Trp Lys Ile Gly Pro Ala Leu Ser Cys Gly Asn
        195                 200                 205

Thr Val Val Lys Pro Ala Glu Gln Thr Pro Leu Thr Ala Leu His
        210                 215                 220

Val Ala Ser Leu Ile Lys Glu Ala Gly Phe Pro Pro Gly Val Val Asn
225                 230                 235                 240

Ile Val Pro Gly Tyr Gly Pro Thr Ala Gly Ala Ala Ile Ser Ser His
            245                 250                 255

Met Asp Ile Asp Lys Val Ala Phe Thr Gly Ser Thr Glu Val Gly Lys
            260                 265                 270

Leu Ile Lys Glu Ala Ala Gly Lys Ser Asn Leu Lys Arg Val Thr Leu
        275                 280                 285
```

```
Glu Leu Gly Gly Lys Ser Pro Cys Ile Val Leu Ala Asp Ala Asp Leu
    290                 295                 300
Asp Asn Ala Val Glu Phe Ala His His Gly Val Phe Tyr His Gln Gly
305                 310                 315                 320
Gln Cys Cys Ile Ala Ala Ser Arg Ile Phe Val Glu Glu Ser Ile Tyr
                325                 330                 335
Asp Glu Phe Val Arg Arg Ser Val Glu Arg Ala Lys Lys Tyr Ile Leu
                340                 345                 350
Gly Asn Pro Leu Thr Pro Gly Val Thr Gln Gly Pro Gln Ile Asp Lys
            355                 360                 365
Glu Gln Tyr Asp Lys Ile Leu Asp Leu Ile Glu Ser Gly Lys Lys Glu
    370                 375                 380
Gly Ala Lys Leu Glu Cys Gly Gly Gly Pro Trp Gly Asn Lys Gly Tyr
385                 390                 395                 400
Phe Val Gln Pro Thr Val Phe Ser Asn Val Thr Asp Glu Met Arg Ile
                405                 410                 415
Ala Lys Glu Glu Ile Phe Gly Pro Val Gln Gln Ile Met Lys Phe Lys
                420                 425                 430
Ser Leu Asp Asp Val Ile Lys Arg Ala Asn Asn Thr Phe Tyr Gly Leu
    435                 440                 445
Ser Ala Gly Val Phe Thr Lys Asp Ile Asp Lys Ala Ile Thr Ile Ser
    450                 455                 460
Ser Ala Leu Gln Ala Gly Thr Val Trp Val Asn Cys Tyr Gly Val Val
465                 470                 475                 480
Ser Ala Gln Cys Pro Phe Gly Gly Phe Lys Met Ser Gly Asn Gly Arg
                485                 490                 495
Glu Leu Gly Glu Tyr Gly Phe His Glu Tyr Thr Glu Val Lys Thr Val
            500                 505                 510
Thr Val Lys Ile Ser Gln Lys Asn Ser
    515                 520
```

(2) INFORMATION FOR SEQ ID NO:3:

(i) SEQUENCE CHARACTERISTICS:
        (A) LENGTH: 2904 base pairs
        (B) TYPE: nucleic acid
        (C) STRANDEDNESS: single
        (D) TOPOLOGY: linear (ii) MOLECULE TYPE: cDNA (iii) HYPOTHETICAL: N (iv) ANTI-SENSE: N (v) FRAGMENT TYPE: N-terminal (ix) FEATURE:
        (A) NAME/KEY: CDS
        (B) LOCATION: 363..2274
        (D) OTHER INFORMATION:

(xi) SEQUENCE DESCRIPTION: SEQ ID NO:3:

```
GAATTCCGGG CGGGAGCCGC CGCGGCAGCG CGGCCGTGGG GTCCGCCGCC GCCGCATCGG      60

AGCGGGAGGA GGAGCAGCGG GGAGGGCGAG GCCGCCGGGC CGAGAGCCGT CCCGCCTGCT     120

CTCGGTCTTC TGCCTTCGCC TCCGCGCGGT GCGTCGGACC CAGGGTCTGT CACCTGGGCG     180

CCAGGGGCCG CCGCCGGGGA GCCGGAGCGG GCAGGACCCT CCCTCCGCCG ACTGCGGCCC     240

GAGAGCGCCC CCGCGGGGTG GAGCGGCAGC CGCCTTCTGC GGGCGGCTGA GTGTCCGTCT     300
```

```
CGCGCCCGGA GCGGGCGACC GCCGTCAGCC CGGAGGAGGA GGAGGAGGAG GAGGGGGCGT      360

CC ATG GGG CTG CTG TCC CAG GGC TCG CCG CTG AGC TGG GAG GAA ACC        407
   Met Gly Leu Leu Ser Gln Gly Ser Pro Leu Ser Trp Glu Glu Thr
    1               5                  10                  15

AAG CGC CAT GCC GAC CAC GTG CGG CGG CAC GGG ATC CTC CAG TTC CTG       455
Lys Arg His Ala Asp His Val Arg Arg His Gly Ile Leu Gln Phe Leu
                20                  25                  30

CAC ATC TAC CAC GCC GTC AAG GAC CGG CAC AAG GAC GTT CTC AAG TGG       503
His Ile Tyr His Ala Val Lys Asp Arg His Lys Asp Val Leu Lys Trp
             35                  40                  45

GGC GAT GAG GTG GAA TAC ATG TTG GTA TCT TTT GAT CAT GAA AAT AAA       551
Gly Asp Glu Val Glu Tyr Met Leu Val Ser Phe Asp His Glu Asn Lys
         50                  55                  60

AAA GTC CGG TTG GTC CTG TCT GGG GAG AAA GTT CTT GAA ACT CTG CAA       599
Lys Val Arg Leu Val Leu Ser Gly Glu Lys Val Leu Glu Thr Leu Gln
     65                  70                  75

GAG AAG GGG GAA AGG ACA AAC CCA AAC CAT CCT ACC CTT TGG AGA CCA       647
Glu Lys Gly Glu Arg Thr Asn Pro Asn His Pro Thr Leu Trp Arg Pro
 80                  85                  90                  95

GAG TAT GGG AGT TAC ATG ATT GAA GGG ACA CCA GGA CAG CCC TAC GGA       695
Glu Tyr Gly Ser Tyr Met Ile Glu Gly Thr Pro Gly Gln Pro Tyr Gly
                100                 105                 110

GGA ACA ATG TCC GAG TTC AAT ACA GTT GAG GCC AAC ATG CGA AAA CGC       743
Gly Thr Met Ser Glu Phe Asn Thr Val Glu Ala Asn Met Arg Lys Arg
                115                 120                 125

CGG AAG GAG GCT ACT TCT ATA TTA GAA GAA AAT CAG GCT CTT TGC ACA       791
Arg Lys Glu Ala Thr Ser Ile Leu Glu Glu Asn Gln Ala Leu Cys Thr
            130                 135                 140

ATA ACT TCA TTT CCC AGA TTA GGC TGT CCT GGG TTC ACA CTG CCC GAG       839
Ile Thr Ser Phe Pro Arg Leu Gly Cys Pro Gly Phe Thr Leu Pro Glu
        145                 150                 155

GTC AAA CCC AAC CCA GTG GAA GGA GGA GCT TCC AAG TCC CTC TTC TTT       887
Val Lys Pro Asn Pro Val Glu Gly Gly Ala Ser Lys Ser Leu Phe Phe
160                 165                 170                 175

CCA GAT GAA GCA ATA AAC AAG CAC CCT CGC TTC AGT ACC TTA ACA AGA       935
Pro Asp Glu Ala Ile Asn Lys His Pro Arg Phe Ser Thr Leu Thr Arg
                180                 185                 190

AAT ATC CGA CAT AGG AGA GGA GAA AAG GTT GTC ATC AAT GTA CCA ATA       983
Asn Ile Arg His Arg Arg Gly Glu Lys Val Val Ile Asn Val Pro Ile
                195                 200                 205

TTT AAG GAC AAG AAT ACA CCA TCT CCA TTT ATA GAA ACA TTT ACT GAG      1031
Phe Lys Asp Lys Asn Thr Pro Ser Pro Phe Ile Glu Thr Phe Thr Glu
        210                 215                 220

GAT GAT GAA GCT TCA AGG GCT TCT AAG CCG GAT CAT ATT TAC ATG GAT      1079
Asp Asp Glu Ala Ser Arg Ala Ser Lys Pro Asp His Ile Tyr Met Asp
225                 230                 235

GCC ATG GGA TTT GGA ATG GGC AAT TGC TGT CTC CAG GTG ACA TTC CAA      1127
Ala Met Gly Phe Gly Met Gly Asn Cys Cys Leu Gln Val Thr Phe Gln
240                 245                 250                 255

GCC TGC AGT ATA TCT GAG GCC AGA TAC CTT TAT GAT CAG TTG GCT ACT      1175
Ala Cys Ser Ile Ser Glu Ala Arg Tyr Leu Tyr Asp Gln Leu Ala Thr
                260                 265                 270

ATC TGT CCA ATT GTT ATG GCT TTG AGT GCT GCA TCT CCC TTT TAC CGA      1223
Ile Cys Pro Ile Val Met Ala Leu Ser Ala Ala Ser Pro Phe Tyr Arg
            275                 280                 285

GGC TAT GTG TCA GAC ATT GAT TGT CGC TGG GGA GTG ATT TCT GCA TCT      1271
Gly Tyr Val Ser Asp Ile Asp Cys Arg Trp Gly Val Ile Ser Ala Ser
        290                 295                 300
```

```
GTA GAT GAT AGA ACT CGG GAG GAG CGA GGA CTG GAG CCA TTG AAG AAC       1319
Val Asp Asp Arg Thr Arg Glu Glu Arg Gly Leu Glu Pro Leu Lys Asn
    305                 310                 315

AAT AAC TAT AGG ATC AGT AAA TCC CGA TAT GAC TCA ATA GAC AGC TAT       1367
Asn Asn Tyr Arg Ile Ser Lys Ser Arg Tyr Asp Ser Ile Asp Ser Tyr
320                 325                 330                 335

TTA TCT AAG TGT GGT GAG AAA TAT AAT GAC ATC GAC TTG ACG ATA GAT       1415
Leu Ser Lys Cys Gly Glu Lys Tyr Asn Asp Ile Asp Leu Thr Ile Asp
                340                 345                 350

AAA GAG ATC TAC GAA CAG CTG TTG CAG GAA GGC ATT GAT CAT CTC CTG       1463
Lys Glu Ile Tyr Glu Gln Leu Leu Gln Glu Gly Ile Asp His Leu Leu
                    355                 360                 365

GCC CAG CAT GTT GCT CAT CTC TTT ATT AGA GAC CCA CTG ACA CTG TTT       1511
Ala Gln His Val Ala His Leu Phe Ile Arg Asp Pro Leu Thr Leu Phe
            370                 375                 380

GAA GAG AAA ATA CAC CTG GAT GAT GCT AAT GAG TCT GAC CAT TTT GAG       1559
Glu Glu Lys Ile His Leu Asp Asp Ala Asn Glu Ser Asp His Phe Glu
385                 390                 395

AAT ATT CAG TCC ACA AAT TGG CAG ACA ATG AGA TTT AAG CCC CCT CCT       1607
Asn Ile Gln Ser Thr Asn Trp Gln Thr Met Arg Phe Lys Pro Pro Pro
400                 405                 410                 415

CCA AAC TCA GAC ATT GGA TGG AGA GTA GAA TTT CGA CCC ATG GAG GTG       1655
Pro Asn Ser Asp Ile Gly Trp Arg Val Glu Phe Arg Pro Met Glu Val
                420                 425                 430

CAA TTA ACA GAC TTT GAG AAC TCT GCC TAT GTG GTG TTT GTG GTA CTG       1703
Gln Leu Thr Asp Phe Glu Asn Ser Ala Tyr Val Val Phe Val Val Leu
                435                 440                 445

CTC ACC AGA GTG ATC CTT TCC TAC AAA TTG GAT TTT CTC ATT CCA CTG       1751
Leu Thr Arg Val Ile Leu Ser Tyr Lys Leu Asp Phe Leu Ile Pro Leu
        450                 455                 460

TCA AAG GTT GAT GAG AAC ATG AAG GTA GCA CAG AAA AGA GAT GCT GTC       1799
Ser Lys Val Asp Glu Asn Met Lys Val Ala Gln Lys Arg Asp Ala Val
465                 470                 475

TTG CAG GGA ATG TTT TAT TTC AGG AAA GAT ATT TGC AAA GGT GGC AAT       1847
Leu Gln Gly Met Phe Tyr Phe Arg Lys Asp Ile Cys Lys Gly Gly Asn
480                 485                 490                 495

GCA GTG GTG GAT GGT TGT GGC AAG GCC CAG AAC AGC ACG GAG CTC GCT       1895
Ala Val Val Asp Gly Cys Gly Lys Ala Gln Asn Ser Thr Glu Leu Ala
                500                 505                 510

GCA GAG GAG TAC ACC CTC ATG AGC ATA GAC ACC ATC ATC AAT GGG AAG       1943
Ala Glu Glu Tyr Thr Leu Met Ser Ile Asp Thr Ile Ile Asn Gly Lys
            515                 520                 525

GAA GGT GTG TTT CCT GGA CTG ATC CCA ATT CTG AAC TCT TAC CTT GAA       1991
Glu Gly Val Phe Pro Gly Leu Ile Pro Ile Leu Asn Ser Tyr Leu Glu
        530                 535                 540

AAC ATG GAA GTG GAT GTG GAC ACC AGA TGT AGT ATT CTG AAC TAC CTA       2039
Asn Met Glu Val Asp Val Asp Thr Arg Cys Ser Ile Leu Asn Tyr Leu
545                 550                 555

AAG CTA ATT AAG AAG AGA GCA TCT GGA GAA CTA ATG ACA GTT GCC AGA       2087
Lys Leu Ile Lys Lys Arg Ala Ser Gly Glu Leu Met Thr Val Ala Arg
560                 565                 570                 575

TGG ATG AGG GAG TTT ATC GCA AAC CAT CCT GAC TAC AAG CAA GAC AGT       2135
Trp Met Arg Glu Phe Ile Ala Asn His Pro Asp Tyr Lys Gln Asp Ser
                580                 585                 590

GTC ATA ACT GAT GAA ATG AAT TAT AGC CTT ATT TTG AAG TGT AAC CAA       2183
Val Ile Thr Asp Glu Met Asn Tyr Ser Leu Ile Leu Lys Cys Asn Gln
            595                 600                 605

ATT GCA AAT GAA TTA TGT GAA TGC CCA GAG TTA CTT GGA TCA GCA TTT       2231
Ile Ala Asn Glu Leu Cys Glu Cys Pro Glu Leu Leu Gly Ser Ala Phe
        610                 615                 620
```

```
AGG AAA GTA AAA TAT AGT GGA AGT AAA ACT GAC TCA TCC AAC T          2274
Arg Lys Val Lys Tyr Ser Gly Ser Lys Thr Asp Ser Ser Asn
    625             630             635

AGACATTCTA CAGAAAGAAA AATGCATTAT TGACGAACTG GCTACAGTAC CATGCCTCTC   2334

AGCCCGTGTG TATAATATGA AGACCAAATG ATAGAACTGT ACTGTTTTCT GGGCCAGTGA   2394

GCCAGAAATT GATTAAGGCT TTCTTTGGTA GGTAAATCTA GAGTTTATAC AGTGTACATG   2454

TACATAGTAA AGTATTTTTG ATTAACAATG TATTTAATA ACATATCTAA AGTCATCATG    2514

AACTGGCTTG TACATTTTTA AATTCTTACT CTGGAGCAAC CTACTGTCTA AGCAGTTTTG   2574

TAAATGTACT GGTAATTGTA CAATACTTGC ATTCCAGAGT TAAAATGTTT ACTGTAAATT   2634

TTTGTTCTTT TAAAGACTAC CTGGGACCTG ATTTATTGAA ATTTTTCTCT TTAAAAACAT   2694

TTTCTCTCGT TAATTTTCCT TTGTCATTTC CTTTGTTGTC TACATTAAAT CACTTGAATC   2754

CATTGAAAGT GCTTCAAGGG TAATCTTGGG TTTCTAGCAC CTTATCTATG ATGTTTCTTT   2814

TGCAATTGGA ATAATCACTT GGTCACCTTG CCCCAAGCTT TCCCCTCTGA ATAAATACCC   2874

ATTGAACTCT GAAAAAAAAA AAAAAAAAA                                    2904

(2) INFORMATION FOR SEQ ID NO:4:

(i) SEQUENCE CHARACTERISTICS:
        (A) LENGTH: 637 amino acids
        (B) TYPE: amino acid
        (D) TOPOLOGY: linear (ii) MOLECULE TYPE: protein (xi) SEQUENCE DESCRIPTION: SEQ ID NO:4:

Met Gly Leu Leu Ser Gln Gly Ser Pro Leu Ser Trp Glu Glu Thr Lys
 1               5                  10                  15

Arg His Ala Asp His Val Arg Arg His Gly Ile Leu Gln Phe Leu His
            20                  25                  30

Ile Tyr His Ala Val Lys Asp Arg His Lys Asp Val Leu Lys Trp Gly
        35                  40                  45

Asp Glu Val Glu Tyr Met Leu Val Ser Phe Asp His Glu Asn Lys Lys
 50                  55                  60

Val Arg Leu Val Leu Ser Gly Glu Lys Val Leu Glu Thr Leu Gln Glu
 65                  70                  75                  80

Lys Gly Glu Arg Thr Asn Pro Asn His Pro Thr Leu Trp Arg Pro Glu
            85                  90                  95

Tyr Gly Ser Tyr Met Ile Glu Gly Thr Pro Gly Gln Pro Tyr Gly Gly
            100                 105                 110

Thr Met Ser Glu Phe Asn Thr Val Glu Ala Asn Met Arg Lys Arg Arg
        115                 120                 125

Lys Glu Ala Thr Ser Ile Leu Glu Glu Asn Gln Ala Leu Cys Thr Ile
    130                 135                 140

Thr Ser Phe Pro Arg Leu Gly Cys Pro Gly Phe Thr Leu Pro Glu Val
145                 150                 155                 160

Lys Pro Asn Pro Val Glu Gly Gly Ala Ser Lys Ser Leu Phe Phe Pro
            165                 170                 175

Asp Glu Ala Ile Asn Lys His Pro Arg Phe Ser Thr Leu Thr Arg Asn
            180                 185                 190

Ile Arg His Arg Arg Gly Glu Lys Val Val Ile Asn Val Pro Ile Phe
        195                 200                 205

Lys Asp Lys Asn Thr Pro Ser Pro Phe Ile Glu Thr Phe Thr Glu Asp
```

-continued

```
            210                 215                 220
Asp Glu Ala Ser Arg Ala Ser Lys Pro Asp His Ile Tyr Met Asp Ala
225                 230                 235                 240

Met Gly Phe Gly Met Gly Asn Cys Cys Leu Gln Val Thr Phe Gln Ala
                245                 250                 255

Cys Ser Ile Ser Glu Ala Arg Tyr Leu Tyr Asp Gln Leu Ala Thr Ile
                260                 265                 270

Cys Pro Ile Val Met Ala Leu Ser Ala Ala Ser Pro Phe Tyr Arg Gly
            275                 280                 285

Tyr Val Ser Asp Ile Asp Cys Arg Trp Gly Val Ile Ser Ala Ser Val
        290                 295                 300

Asp Asp Arg Thr Arg Glu Glu Arg Gly Leu Glu Pro Leu Lys Asn Asn
305                 310                 315                 320

Asn Tyr Arg Ile Ser Lys Ser Arg Tyr Asp Ser Ile Asp Ser Tyr Leu
                325                 330                 335

Ser Lys Cys Gly Glu Lys Tyr Asn Ile Asp Leu Thr Ile Asp Lys
                340                 345                 350

Glu Ile Tyr Glu Gln Leu Leu Gln Glu Gly Ile Asp His Leu Leu Ala
            355                 360                 365

Gln His Val Ala His Leu Phe Ile Arg Asp Pro Leu Thr Leu Phe Glu
    370                 375                 380

Glu Lys Ile His Leu Asp Asp Ala Asn Glu Ser Asp His Phe Glu Asn
385                 390                 395                 400

Ile Gln Ser Thr Asn Trp Gln Thr Met Arg Phe Lys Pro Pro Pro Pro
                405                 410                 415

Asn Ser Asp Ile Gly Trp Arg Val Glu Phe Arg Pro Met Glu Val Gln
                420                 425                 430

Leu Thr Asp Phe Glu Asn Ser Ala Tyr Val Val Phe Val Leu Leu
            435                 440                 445

Thr Arg Val Ile Leu Ser Tyr Lys Leu Asp Phe Leu Ile Pro Leu Ser
        450                 455                 460

Lys Val Asp Glu Asn Met Lys Val Ala Gln Lys Arg Asp Ala Val Leu
465                 470                 475                 480

Gln Gly Met Phe Tyr Phe Arg Lys Asp Ile Cys Lys Gly Gly Asn Ala
                485                 490                 495

Val Val Asp Gly Cys Gly Lys Ala Gln Asn Ser Thr Glu Leu Ala Ala
            500                 505                 510

Glu Glu Tyr Thr Leu Met Ser Ile Asp Thr Ile Ile Asn Gly Lys Glu
        515                 520                 525

Gly Val Phe Pro Gly Leu Ile Pro Ile Leu Asn Ser Tyr Leu Glu Asn
    530                 535                 540

Met Glu Val Asp Val Asp Thr Arg Cys Ser Ile Leu Asn Tyr Leu Lys
545                 550                 555                 560

Leu Ile Lys Lys Arg Ala Ser Gly Glu Leu Met Thr Val Ala Arg Trp
                565                 570                 575

Met Arg Glu Phe Ile Ala Asn His Pro Asp Tyr Lys Gln Asp Ser Val
            580                 585                 590

Ile Thr Asp Glu Met Asn Tyr Ser Leu Ile Leu Lys Cys Asn Gln Ile
        595                 600                 605
```

```
                                            -continued

Ala Asn Glu Leu Cys Glu Cys Pro Glu Leu Leu Gly Ser Ala Phe Arg
        610             615             620

Lys Val Lys Tyr Ser Gly Ser Lys Thr Asp Ser Ser Asn
625             630             635
```